United States Patent
Sheppard, Jr. et al.

(10) Patent No.: US 10,473,582 B2
(45) Date of Patent: Nov. 12, 2019

(54) COMBINATION OPTICAL HEMOGLOBIN AND ELECTROCHEMICAL LEAD ASSAY

(71) Applicant: Magellan Diagnostics, Inc., North Billerica, MA (US)

(72) Inventors: Norman F. Sheppard, Jr., New Ipswich, NH (US); Gary Conrad Jensen, Cambridge, MA (US)

(73) Assignee: Magellan Diagnostics, Inc., North Billerica, MA (US)

( * ) Notice: Subject to any disclaimer, the term of this patent is extended or adjusted under 35 U.S.C. 154(b) by 0 days.

(21) Appl. No.: 15/701,006

(22) Filed: Sep. 11, 2017

(65) Prior Publication Data
US 2018/0059010 A1 Mar. 1, 2018

Related U.S. Application Data

(63) Continuation of application No. 14/978,292, filed on Dec. 22, 2015, now Pat. No. 9,759,651.
(Continued)

(51) Int. Cl.
*G01N 21/31* (2006.01)
*G01N 33/49* (2006.01)
*G01N 21/47* (2006.01)

(52) U.S. Cl.
CPC .......... *G01N 21/31* (2013.01); *G01N 21/474* (2013.01); *G01N 33/49* (2013.01);
(Continued)

(58) Field of Classification Search
CPC ...... G01N 21/31; G01N 33/49; G01N 21/474; G01N 2201/0696; G01N 2201/062; G01N 2201/0625; G01N 27/4166; G01N 27/30
See application file for complete search history.

(56) References Cited

U.S. PATENT DOCUMENTS 3,569,721 A 3/1971 Goldberg et al.
3,874,799 A 4/1975 Isaacs
(Continued)

FOREIGN PATENT DOCUMENTS

EP 0549970 A1 7/1993

OTHER PUBLICATIONS

International Search Report dated Mar. 2, 2017 in corresponding International Application No. PCT/US2016/069290, filed Dec. 29, 2016.
(Continued)

*Primary Examiner* — Mohamed K Amara
(74) *Attorney, Agent, or Firm* — Knobbe Martens Olson & Bear LLP

(57) ABSTRACT

A sensor and analyzer for measuring an analyte in a liquid sample are disclosed. The sensor includes a substrate with a reservoir disposed therein. The reservoir may include a top surface and a bottom surface, at least one transparent portion forming at least a part of the bottom surface of the reservoir, and a reflector disposed on the upper surface of the reservoir at a location opposite the at least one transparent portion. The analyzer may include a support surface, an aperture extending through the support surface, a light source disposed below the support surface and oriented so that at least a portion of the light emitted from the light source passes through the aperture, and a detector configured to measure an intensity of light received at the detector.

7 Claims, 19 Drawing Sheets

Related U.S. Application Data

(60) Provisional application No. 62/096,178, filed on Dec. 23, 2014.

(52) U.S. Cl.
CPC ............... *G01N 2201/062* (2013.01); *G01N 2201/0625* (2013.01); *G01N 2201/0696* (2013.01)

(56) References Cited

U.S. PATENT DOCUMENTS

| | | | |
|---|---|---|---|
| 4,069,017 A | 1/1978 | Wu et al. | |
| 4,412,005 A | 10/1983 | Wu | |
| 4,788,153 A | 11/1988 | Detwiler et al. | |
| 4,816,224 A | 3/1989 | Vogel et al. | |
| 5,039,491 A | 8/1991 | Saaski | |
| 5,049,487 A | 9/1991 | Phillips | |
| 5,368,707 A | 11/1994 | Henkens et al. | |
| 5,468,366 A | 11/1995 | Wegner et al. | |
| 5,485,276 A * | 1/1996 | Bien | G01N 21/031 250/576 |
| 5,739,432 A | 4/1998 | Sinha | |
| 5,873,990 A | 2/1999 | Wojciechowski et al. | |
| 6,466,316 B2 | 10/2002 | Modlin | |
| 6,549,275 B1 | 4/2003 | Cabuz | |
| 6,551,842 B1 | 4/2003 | Carpenter | |
| 6,809,826 B2 | 10/2004 | Robertson | |
| 6,897,069 B1 | 5/2005 | Jarvis | |
| 7,215,428 B2 * | 5/2007 | McNeal | G01N 21/031 356/246 |
| 7,352,464 B2 * | 4/2008 | Chen | G01N 21/3504 356/437 |
| 7,397,036 B2 | 7/2008 | Robertson | |
| 7,623,225 B2 | 11/2009 | Robertson, Jr. | |
| 7,636,162 B2 | 12/2009 | Ogawa | |
| 7,840,246 B1 | 11/2010 | Poore | |
| 8,189,199 B2 | 5/2012 | Robertson, Jr. | |
| 8,208,145 B2 | 6/2012 | Large | |
| 8,486,689 B2 * | 7/2013 | Bruls | G01N 21/1717 435/283.1 |
| 8,730,468 B2 * | 5/2014 | Messerchmidt | G01N 21/43 356/300 |
| 8,970,838 B2 * | 3/2015 | Messerschmidt | G01N 21/65 356/301 |
| 9,036,153 B1 * | 5/2015 | Gupta | G01N 21/55 356/237.2 |
| 9,513,224 B2 * | 12/2016 | Mohan | G01N 21/0303 |
| 9,557,268 B2 * | 1/2017 | Morrow | G01N 21/64 |
| 9,562,860 B1 * | 2/2017 | Pangarkar | G01N 21/6428 |
| 2001/0048899 A1 | 12/2001 | Marouiss | |
| 2002/0009391 A1 | 1/2002 | Marquiss et al. | |
| 2002/0140940 A1 | 10/2002 | Bambot | |
| 2004/0019462 A1 * | 1/2004 | Gehrlein | B01F 3/02 702/188 |
| 2005/0250217 A1 | 11/2005 | Keenan | |
| 2006/0043301 A1 * | 3/2006 | Mantele | G01N 21/05 250/339.11 |
| 2006/0091006 A1 | 5/2006 | Wang et al. | |
| 2006/0187459 A1 * | 8/2006 | Ok | B01L 3/502715 356/445 |
| 2007/0081163 A1 * | 4/2007 | Liang | G01N 21/253 356/445 |
| 2007/0212259 A1 | 9/2007 | Fujimura | |
| 2007/0299385 A1 | 12/2007 | Santini, Jr. | |
| 2008/0006202 A1 | 1/2008 | Hirano | |
| 2008/0213875 A1 | 9/2008 | Sharrock | |
| 2009/0257064 A1 * | 10/2009 | Tkachuk | G01J 3/42 356/453 |
| 2010/0010325 A1 | 1/2010 | Ridder | |
| 2010/0195098 A1 | 8/2010 | Zuo | |
| 2010/0259254 A1 * | 10/2010 | Verschuren | G01N 15/06 324/244 |
| 2010/0277742 A1 | 11/2010 | McMillan | |
| 2010/0323669 A1 | 12/2010 | Myrick | |
| 2011/0057120 A1 | 3/2011 | Ostendarp | |
| 2011/0188030 A1 * | 8/2011 | Verschuren | G01N 21/41 356/128 |
| 2011/0211189 A1 | 9/2011 | Ryan | |
| 2011/0299076 A1 * | 12/2011 | Feitisch | G01J 3/28 356/326 |
| 2012/0057164 A1 | 3/2012 | Tezuka | |
| 2012/0088486 A1 * | 4/2012 | Messerchmidt | G01J 3/02 455/418 |
| 2013/0043405 A1 | 2/2013 | Maxwell | |
| 2013/0098163 A1 | 4/2013 | Tarasev | |
| 2013/0109938 A1 | 5/2013 | Kuhn | |
| 2013/0242308 A1 | 9/2013 | Zhan | |
| 2013/0330230 A1 | 12/2013 | Uri | |
| 2014/0080172 A1 | 3/2014 | Tunheim | |
| 2014/0160474 A1 * | 6/2014 | Keller | G01N 21/3504 356/246 |
| 2014/0251836 A1 | 9/2014 | Feeney | |
| 2015/0062572 A1 * | 3/2015 | Tharaldsen | G01J 3/021 356/300 |
| 2015/0125899 A1 | 5/2015 | Willits | |
| 2015/0132789 A1 | 5/2015 | Bornheimer | |
| 2015/0233760 A1 | 8/2015 | Kielhorn | |
| 2015/0369725 A1 * | 12/2015 | Carvalho Sousa | A61B 5/14532 435/288.7 |
| 2016/0047685 A1 * | 2/2016 | Blei | A61M 5/31551 250/227.11 |
| 2016/0054177 A1 | 2/2016 | Feitisch | |
| 2016/0103089 A1 | 4/2016 | Boyette | |
| 2016/0109367 A1 | 4/2016 | Jasperse | |
| 2016/0169842 A1 | 6/2016 | Yamamoto | |
| 2016/0178573 A1 | 6/2016 | Sheppard, Jr. et al. | |
| 2016/0299061 A1 * | 10/2016 | Goldring | G01J 3/0291 |

OTHER PUBLICATIONS

Agilent Technologies (Agilent Cary 7000 Universal Measurement Spectrophotometer. 2013. pp. 1-12).

Akobeng, "Neonatal jaundice," *Am. Fam Physician*, 2005, 71(5):947-948.

Kazmierczak et al. (Direct Spectrophotometric Method for Measurement of Bilirubin in Newborns: Comparison with HPLC and an Automated Diazo Method. Clinical Chemistry 2002 pp. 1096-1097).

Lamola et al. Neonatal bilirubin binding capacity discerns risk of neurological dysfunction. Pediatric Research vol. 77, pp. 334-339 (epub Nov. 24, 2014).

* cited by examiner

COMBINATION OPTICAL HEMOGLOBIN AND ELECTROCHEMICAL LEAD ASSAY

INCORPORATION BY REFERENCE TO ANY PRIORITY APPLICATIONS

This application claims is a continuation of U.S. application Ser. No. 14/978,292, filed Dec. 22, 2015, which claims priority to U.S. Provisional Application No. 62/096,178, filed Dec. 23, 2014, both of which are incorporated herein by reference. Any and all applications for which a foreign or domestic priority claim is identified in the Application Data Sheet as filed with the present application are hereby incorporated by reference under 37 CFR 1.57.

BACKGROUND

Field

This disclosure relates to a sensor, analyzer, and method for analyzing at least one analyte in sample.

Description

It is frequently desired to analyze the amount of an analyte in a liquid sample, such as blood or other biological fluids. When sampling analytes in blood, it may be desirable to sample for more than one analyte. This may require using a separate sensor, reagent, and/or sampling apparatus for each analyte. However, using a separate sensor, reagent, and/or sampling apparatus may be time consuming and costly. Therefore, a sensor which can detect and/or measure the concentration of two analytes in a single sampling operation may be desired.

Electrochemical stripping and square wave voltammetry techniques have been developed using colloidal gold based sensors to measure concentrations of various analytes, such as lead, in a blood sample. Some exemplary techniques and apparatuses are described in U.S. Pat. No. 5,873,990, entitled "Handheld Electromonitor Device," the entirety of which is incorporated herein by reference. These techniques allow for low cost, quick, and accurate testing of blood lead concentration; they do not, however, test for any additional analytes.

A correlation between the color of blood samples treated with hydrochloric acid and hemoglobin concentration has long been observed. The Sahli hemoglobin method, developed in the early 1900s and still used today in some parts of the world, estimates blood hemoglobin concentration by matching the color of treated blood to predetermined samples and/or color standards. This method however, remains imprecise and fails to test for any additional analytes.

SUMMARY

In one aspect, a sensor for measuring an analyte in a liquid sample is disclosed. The sensor includes a reservoir having a top surface and a bottom surface, at least one transparent portion forming at least a part of the bottom surface of the reservoir, and a portion of the top surface that comprises a reflector.

In some embodiments, the substrate further comprises a base layer forming the bottom surface of the reservoir, wherein the at least one transparent portion forms at least a portion of the base layer; a first spacer layer having a first void extending through a thickness of the first spacer layer; a second spacer layer having a second void extending through a thickness of the second spacer layer and wherein at least a portion of a bottom surface of the second spacer layer comprises the portion of the top surface of the reservoir comprising the reflector; a lid having a bottom surface, and wherein at least a portion of the bottom surface of the lid forms at least a portion of the top surface of the reservoir. The first spacer layer is disposed on the base layer, the second spacer layer is disposed on the first spacer layer, and the lid is disposed on the second spacer layer. In some embodiments, the reservoir further comprises a first depth between the bottom surface of the reservoir and a first portion of the upper surface of the reservoir, and a second depth between the bottom surface of the reservoir and a second portion of the upper surface of the reservoir, wherein the first depth is less than the second depth, and wherein the reflector is disposed on the first portion of the upper surface of the reservoir. In some embodiments, the first depth is equal to the thickness of the first spacer layer, and the second depth is equal to a combined thickness of the thickness of the first spacer layer and the thickness of the second spacer layer. In some embodiments, the first depth and the second depth may also include a thickness of one or more adhesive layers. In some embodiments, the sensor is configured to be used to analyze for a hemoglobin concentration of the liquid sample using an optical measurement.

In some embodiments, the sensor may further comprise at least one electrode disposed on a bottom surface of the reservoir and at least one electrical contact disposed on the base layer, wherein the at least one electrode is in electrical communication with the at least one electrical contact. In some embodiments, a first of the at least one electrodes comprises a colloidal gold deposit. In some embodiments, the sensor is configured to be used to analyze for a hemoglobin concentration of the liquid sample using an optical measurement and to analyze for lead concentration using an electrochemical measurement. In some embodiments, the liquid sample is a blood sample treated with hydrochloric acid.

In a second aspect, an analyzer for measuring an analyte in a liquid sample is disclosed. The analyzer comprises a port for receiving a sensor and having a support surface configured to support the sensor, an aperture extending through the support surface, a light source disposed below the support surface and oriented so that at least a portion of the light emitted from the light source passes through the aperture, a detector configured to measure an intensity of light received at the detector; and a processor electrically coupled to the detector to receive an output of the detector.

In some embodiments, the analyzer further comprises a window disposed within the aperture. In some embodiments, the window comprises sapphire. In some embodiments, the detector is disposed below the support surface of the analyzer. In some embodiments, the light source comprises first and second light sources, and the first and second light sources are configured to alternatingly emit light. In some embodiments, the first and second light sources further comprise integrated lenses configured to focus the light emitted through the aperture. In some embodiments, the first and second light sources are configured so that the light emitted from each passes through the aperture at an approximately 45° angle relative to a central axis of the aperture. In some embodiments, the light source and detector are configured to emit and detect light at a wavelength corresponding to an isosbestic point of the liquid sample. In some embodiments, the light source and detector are configured to emit and detect light with a wavelength of approximately 405 nm which represents an isosbestic point of a blood sample treated with hydrochloric acid. In some embodiments, the analyzer further comprises a clock, the clock electrically connected to the light source and the detector, and configured so that the light source can be pulsed at a first frequency and the detector can be demodulated at the first frequency.

In some embodiments, the analyzer is configured to make a first optical measurement of light reflected off a reflector of the sensor before the liquid sample is introduced and a second optical measurement of light reflected off a reflector of the sensor after the liquid sample is introduced.

In a third aspect, a method for measuring an analyte in a liquid sample is disclosed. The method comprises inserting a sensor into an analyzer; introducing the liquid sample to a reservoir in the sensor, illuminating the liquid sample in the sensor using a light source in the analyzer, measuring a reflectance of the liquid sample using a detector in the analyzer, and computing a measurement of the analyte using the measured reflectance.

In some embodiments, the reflectance is measured by measuring light reflected off a reflective surface in the sensor. In some embodiments, the reflectance is computed by comparing an intensity measured at the detector to a reference intensity. In some embodiments, the reference intensity is obtained by inserting an empty sensor into the analyzer, illuminating the empty sensor, and measuring an intensity of light received at the detector. In some embodiments, internally reflected stray light is measured by detecting at the detector the intensity of light reflected off a light absorbing surface as the sensor is inserted into or withdrawn from the analyzer, and the method further comprises subtracting the measured internally reflected stray light from the reference intensity and the measured intensity of the sample to obtain a result which corrects for internally reflected stray light.

In some embodiments, the measured analyte is hemoglobin and the liquid sample comprises a blood sample treated with hydrochloric acid. In some embodiments, the method further comprises making an electrochemical measurement of lead using the same sensor and analyzer.

DETAILED DESCRIPTION

Figure 1:
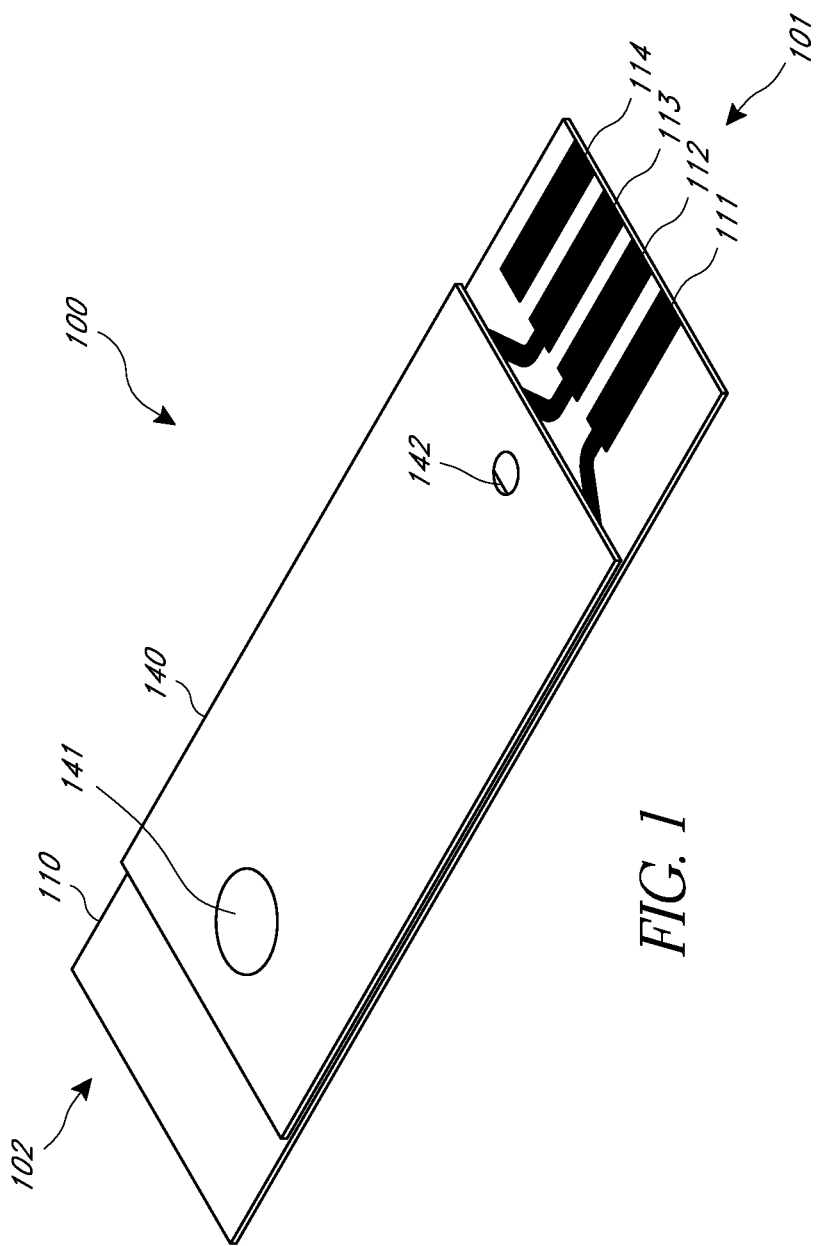
FIG. 1 depicts a perspective view of an embodiment of a combination electrochemical lead and optical hemoglobin sensor.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are intended to be within the scope of this disclosure.

Disclosed in the present application are a sensor, analyzer, system, and methods for analyzing a sample for at least one analyte. In some embodiments, the sample is a vertebrate or mammalian blood sample, and the sample is placed on the sensor of the present disclosure, the sensor being readable using the analyzer. In some embodiments, the sample may be treated with a reagent to facilitate the analysis. In some embodiments, the reagent is hydrochloric acid. In some embodiments, the sample is analyzed for hemoglobin concentration and results may be provided to a user in grams of hemoglobin per deciliter of sample (g/dL). In some embodiments, the sample is analyzed for lead concentration and hemoglobin concentration. A single sensor may be used to analyze the sample for lead concentration using an electrochemical measurement and may further be used to analyze the sample for hemoglobin concentration using an optical measurement. A sensor having a substrate suitable for use in sampling blood lead levels is described in U.S. Pat. No. 5,468,366, entitled "Colloidal-Gold Electrosensor Measuring Device," the entire contents of which are herein incorporated by reference. Blood lead concentration analysis can be performed using systems and methods similar to those described in U.S. Pat. No. 5,873,990, referenced above.

As used herein, the terms "simultaneously" or "at the same time" need not necessarily mean at exactly the same moment, and may mean that two actions or operations occur concurrently. For example, in the following disclosure reference is made to analyzing lead concentration and hemoglobin concentration at the same time or simultaneously. This need not mean that the sensors or sampling apparatus are performing the analysis at exactly the same moment, or that electrical or optical signals are applied to the sensing electrodes or detectors of the sensor at exactly the same instant. Simultaneous measurement or measurement "at the same time" of lead and hemoglobin may mean that lead and hemoglobin are measured using a single sensor and sampling apparatus, or by testing the same blood sample, possibly with little to no need for operator intervention between the analyses. The measurement of lead and hemoglobin may occur sequentially, such as lead measurement first, and then hemoglobin measurement, or vice versa, at generally the same time, or within a short time window. In some embodiments, the sensor may be used to make only a single measurement of one analyte.

FIG. 1 depicts an embodiment of a combination electrochemical lead and optical hemoglobin sensor configured to receive a liquid sample and facilitate analysis of at least one analyte in the sample. The sensor 100 is generally rectangular in shape and may comprise base layer 110 and a lid layer 140 disposed on the base layer. Lid layer 140 includes a sample inlet 141 and a vent 142, each formed as holes that extend through a thickness of lid layer 140. In some embodiments, other layers may be disposed between base layer 110 and lid layer 140. Sensor 100 may further comprise an overall length dimension measured between the first end 101 and second end 102 along a line perpendicular to first end 101; an overall width dimension, measured along first end 101 or second end 102; and an overall thickness dimension, measured between a top surface of lid layer 140 and a bottom surface of base layer 110 along a line normal to a top surface of lid layer 140. In some embodiments, the overall length dimension is about 1.72" the overall width dimension is about 0.55", and the overall thickness dimension is about 0.031". It will be understood by one of skill in the art, according to the principles and embodiments presently disclosed, that other dimensions are possible and within the scope of the present disclosure. For example, in some embodiments the overall length dimension is between about 0.5" and about 6", the overall width dimension is between about 0.25" and about 3", and the overall thickness is between about 0.005" and about 0.5"; however, other sizes outside of these ranges are possible and contemplated. Further, it should be noted that other shapes, besides rectangular, may be used according to the principles and subject matter presently disclosed. For example, in some embodiments, sensor 100 may be substantially circular. In some embodiments, the dimensions of the sensor may correspond to a sensor port on an analyzer which will be described in greater detail below.

In some embodiments, sensor 100 comprises first end 101 and second end 102. First end 101 includes a plurality of contacts 111-114 and is configured in size and shape to be insertable into a sample port on an analyzer, wherein the sample port has a compatible geometry configured to receive first end 101 of sensor 100. In some embodiments, the cross section of the sensor 100 and the sample port are substantially rectangular. Contacts 111-114 will be discussed in greater detail below. In some embodiments, sensor 100 is configured so that second end 102 remains exposed when first end 101 has been inserted into the analyzer. This may allow a user to introduce the liquid sample to sensor 100 after sensor 100 has been inserted into the analyzer.

Figure 2:
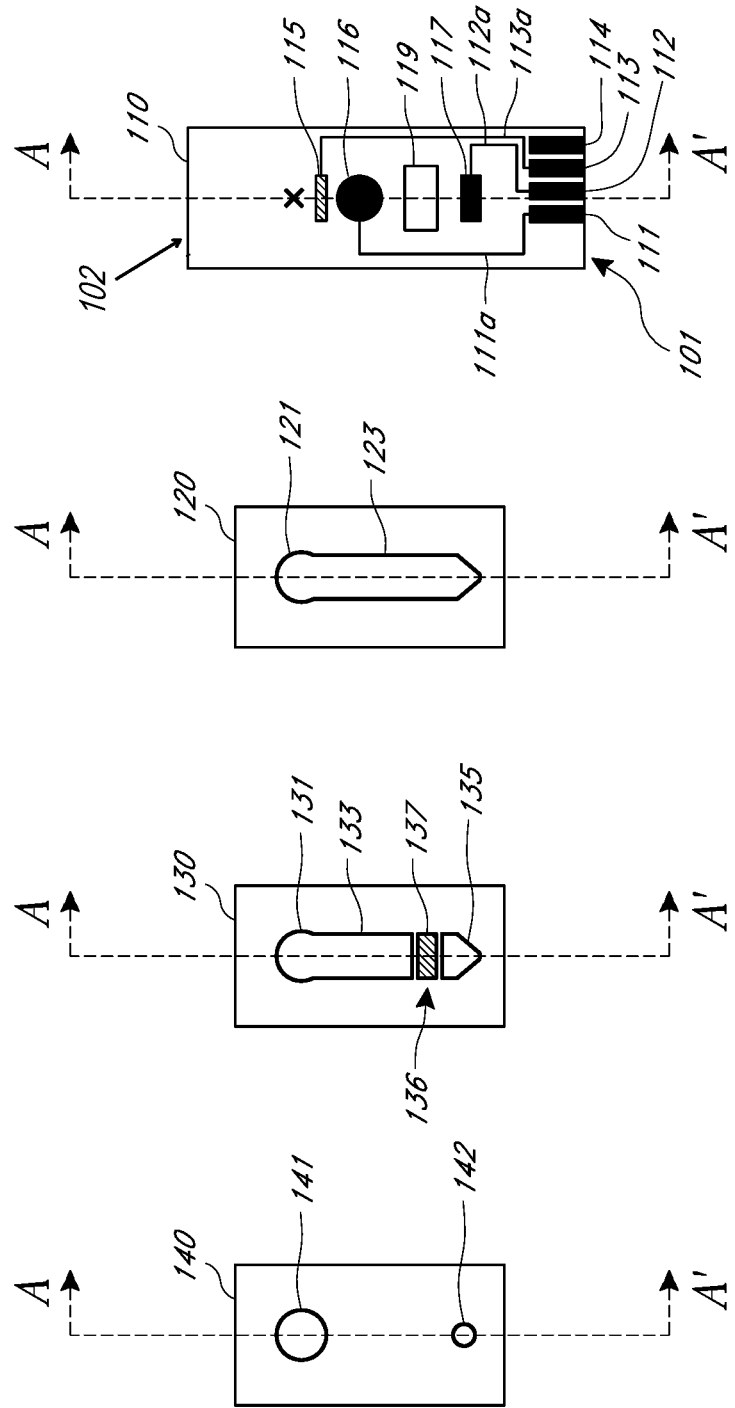
FIG. 2 depicts each of the layers individually of an embodiment of a combination electrochemical lead and optical hemoglobin sensor.

Referring now to FIG. 2, sensor 100 includes several layers stacked on top of each other to form the various features of sensor 100. Sensor 100 may comprise a base layer 110, a first spacer layer 120, a second spacer layer 130, and a lid layer 140. A thin layer of adhesive may be applied between each successively stacked layer, bonding the layers together to form sensor 100. In some embodiments, each layer of adhesive is approximately 0.001 inches thick, although it will be understood by one of skill in the art that different thicknesses may be used. In some embodiments, bonding methods other than adhesive may be used, or sensor 100 may be manufactured or formed as a unitary piece, either through printing, molding, or other suitable manufacturing process.

Each layer of sensor 100 will now be described in greater detail with reference to FIG. 2, which depicts embodiments of each of the layers individually for convenience and ease of description. In some embodiments, base layer 110 is generally rectangular in shape having a length of approximately 1.72" a width of approximately 0.55", and a thickness of approximately 0.01"; it will be understood by one of skill in the art, however, that other dimensions for the base layer may be used. In some embodiments the length of base 110 extends beyond the other layers in a longitudinal direction, each end of base layer 110 forming one of first end 101 and second end 102 of sensor 100.

Base layer 110 may comprise a transparent substrate that permits optical signals to pass there through. In some embodiments, the base layer 110 is formed entirely of a transparent material. In some embodiments, base layer 110 is only partially comprised of a transparent material, the transparent material forming a transmission window 119 through the base layer 110 to allow for optical interrogation of a sample. In some embodiments, the transmission window 119 is disposed between a working electrode 116 and a counter electrode 117 along a longitudinal axis of base layer 110. The optically transparent material of base layer 110 may be formed from plastic, glass, or other suitable material that permits light of the wavelengths discussed below to be transmitted there through. In some embodiments, at least the transmission window 119 of the base layer 110 is made from polycarbonate or polyester. In some embodiments of base layer 110 a hard-coated, optical grade polycarbonate with a gloss finish is used for the transmission window 119.

The components used to make an electrochemical measurement of the lead concentration of a liquid sample are disposed on an upper surface of base layer 110. These include contacts 111-114, traces 111a-113a, and electrodes 115-117. In some embodiments, the contacts 111-114 and traces 111a-113a are a silver-containing material screen printed onto base layer 110. In some embodiments, contacts 111-114 and traces 111a-113a include a carbon layer screen printed on top of the silver layer. In some embodiments, the contacts and electrical traces may be printed, etched, or otherwise deposited on the base layer 110.

In the illustrated embodiment, sensor 100 includes four contacts: a working electrode contact 111, an auxiliary or counter electrode contact 112, a reference electrode contact 113, and a sensor insertion contact 114. The contacts 111-114 are disposed on first end 101 of sensor 100 on an upper surface of base layer 110, and are exposed such that upon insertion of sensor 100 into a sample port of an analyzer, the contacts 111-114 make physical contact with corresponding contacts in the analyzer forming an electrical connection between sensor 100 and the analyzer.

Each of contacts 111-113 is in electrical communication with traces 111a-113a, respectively, the traces 111a-113a extending generally away from the first end 101 of sensor 100 and toward the second end 102 of sensor 100. Through trace 111a, the working electrode contact 111 is in electrical contact with the working electrode 116. Through trace 112a, the counter electrode contact 112 is in electrical contact with the counter electrode 117. Through trace 113a, reference electrode contact 113 is in electrical contact with the reference electrode 115. Although one configuration is depicted in FIG. 2 for the electric traces and the contacts, one of skill in the art will understand that a different contact order or trace configuration can be used without departing from the scope of the present application (see, for example, FIGS. 3A and 3B).

Working electrode 116 is disposed on an upper surface of base 110 and includes a layer of carbon which has been sputtered, printed, sprayed, air brushed, or otherwise deposited on base layer 110. The working electrode may also advantageously comprise a colloidal gold solution sputtered, printed, sprayed, air brushed, or otherwise deposited on the carbon layer. The counter electrode 117 is similarly disposed on base layer 110. Counter electrode 117 may be comprised of carbon and may be formed through the same processes described in reference to the working electrode 116. Reference electrode 115 may comprise carbon, silver, or silver chloride and is similarly disposed on base layer 110. Electrodes 115-117 are disposed on an upper surface of base layer 110 so as to come into contact with a sample in the sensor 100. It will be appreciated by one of skill in the art that the particular arrangement, order, material of construction, and/or number of the electrodes 115-117 may vary without departing from the scope of the present disclosure. The function of each electrode 115-117 is discussed elsewhere.

The first spacer layer 120 is disposed on an upper surface of base layer 110. First spacer layer 120 may also be generally rectangular in shape with a width less than or equal to the width of the base layer 110 and a length less than the length of base layer 110. First spacer layer 120 may advantageously be about 0.002" thick, and include a 0.001" thick layer of adhesive on each side for a total thickness of about 0.004"; although one of skill in the art will understand according to the present disclosure that other thicknesses may be used, for example, thicknesses of approximately 0.0005", 0.001", 0.005", 0.010", or any thickness there between. As will be described in greater detail below with regard to FIGS. 5A-5B, the thickness of the first spacer layer 120 affects the path length of light traveling through the sample and affects the amount of light available for detection.

First spacer layer 120 is disposed on top of base layer 110 so that the contacts 111-114, also disposed on base layer 110, remain exposed. As seen in FIG. 2, first spacer layer 120 includes a first sample reservoir space 123 that is formed as a void in first spacer layer 120. The first sample reservoir space 123 is configured in size and shape to surround the electrodes 115-117 when both the first spacer layer 120 and the electrodes 115-117 are disposed on base layer 110. First spacer layer 120 may also include an inlet portion 121 configured in size and shape to align with sample inlet 141 when sensor 100 is fully assembled. The first spacer layer 120 may comprise an electrically insulating material, such as Mylar®, or other similar material. In some embodiments, the material may be hydrophilic, or coated with a hydrophilic substance.

The second spacer layer 130 is disposed on top of the first spacer layer 120. Second spacer layer 130 may have the same width and length dimensions as the first spacer layer 120. Second spacer layer 130 may be made from white polyester or any other suitable material. In some embodiments, a suitable material may be one that can be used as a diffuse reflector. In some embodiments, the material may be hydrophilic, or coated with a hydrophilic substance. The combined thickness of first spacer layer 120 and second spacer layer 130 defines a depth of a reservoir within sensor 100 that allows electrodes 115-117 to be used to make an electrochemical measurement of lead concentration. This depth will be discussed in greater detail below with reference to FIGS. 5A-5B. In some embodiments the second spacer layer 130 is approximately 0.001, 0.005, 0.01, 0.15, 0.2 inches thick or more, or any thickness therebetween. The thickness of the second spacer layer 130 affects the volume of sample, such as blood, which is accommodated on the sensor. A person of skill in the art, guided by the present disclosure, will understand how to vary the thickness of the first spacer layer 120 and the second spacer layer 130 in order to obtain an electrochemical lead measurement at the working electrode 115.

In some embodiments, second spacer layer 130 includes a second sample reservoir space 133 and a third sample reservoir space 135, each formed as voids in second spacer 130. Second and third sample reservoir spaces 133, 135 are separated by a bridge 136. The bridge 136 includes the portion of the second spacer layer 130 located between the second and third reservoirs 133 and 135, and may be formed as an integral piece of the second spacer layer 130.

Figure 5A:
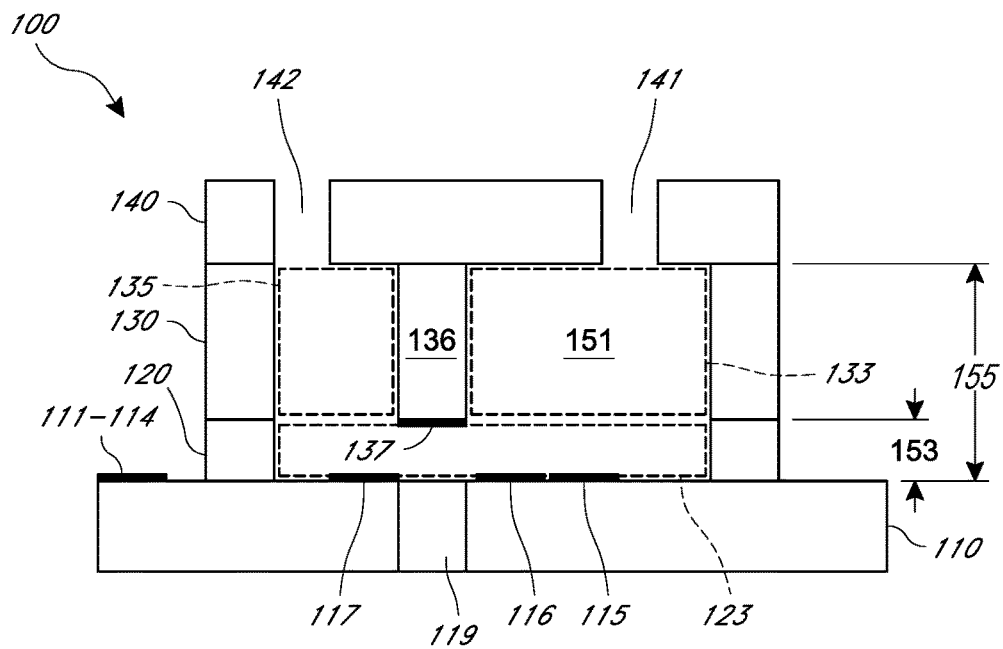
FIGS. 5A and 5B depict simplified longitudinal cross-section views of embodiments of a combination electrochemical lead and optical hemoglobin sensor taken along the line A-A' in FIGS. 2 and 4.

In some embodiments, the bridge 136 itself may comprise the reflector 137; for example, when second spacer layer 130 including bridge 136 is made from white polyester, which itself acts as a diffuse reflector, no additional reflector is needed. When second spacer layer 130 is assembled on top of first spacer layer 120, the second sample reservoir space 133 and the third sample reservoir space 135 are in fluid communication with each other by means of the first sample reservoir space 123 of the first spacer layer 120, as shown in FIG. 5A. Second spacer layer 130 may also include an inlet portion 131 configured in size and shape to align with sample inlet 141 when sensor 100 is fully assembled.

A lid layer 140 is disposed on top of second spacer layer 130. The lid layer 140 is configured in size and shape to have the same width and length dimensions as second spacer layer 130. In some embodiments, lid layer 140 is about 0.001, 0.005, 0.01, 0.02 inches thick or more, or any value there between. Lid layer 140 may be comprised of a plastic or other suitable material. In some embodiments, lid layer 140 is coated with a hydrophilic substance so that the reservoir can be more easily filled with the sample. In some embodiments, lid layer 140 may also be formed of a clear, transparent, or translucent material which provides a visual indication to the user when the reservoir is filled. In some embodiments, lid layer 140 may be opaque so as to shield the optical measurements that will be discussed below from interference from ambient light. It will be noted, however, that a clear lid layer 140 may be used and obtain an accurate optical measurement according to the present disclosure. The lid layer 140 provides an upper boundary on a sample reservoir within sensor 100 to prevent evaporation of the sample. Lid layer 140 also includes a sample inlet 141 and a vent 142 formed as voids extending through a thickness of the lid layer 140. The relative positioning of the inlet 141 and vent 142 depicted in FIG. 2 is merely illustrative and one of skill in the art will appreciate that the positioning of the inlet 141 and vent 142 may vary without departing from the scope of the present disclosure.

Figure 3A:
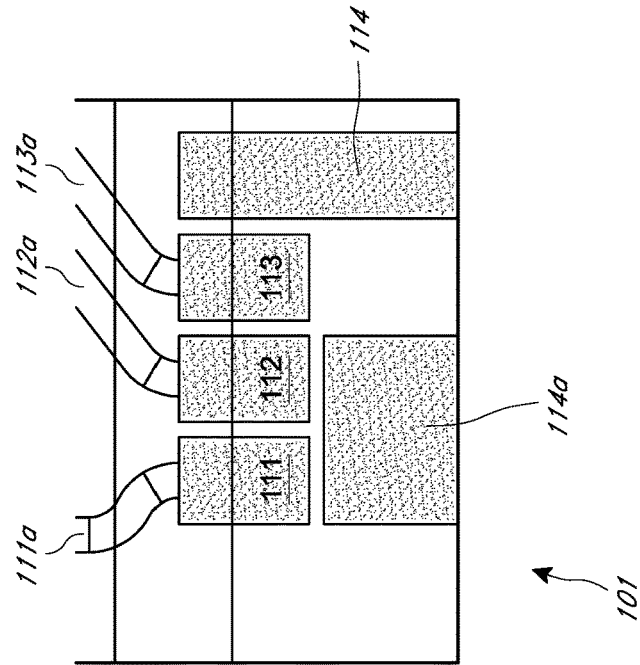
FIGS. 3A and 3B depict embodiments of electrical contacts disposed on a base layer of a sensor.
Figure 3B:
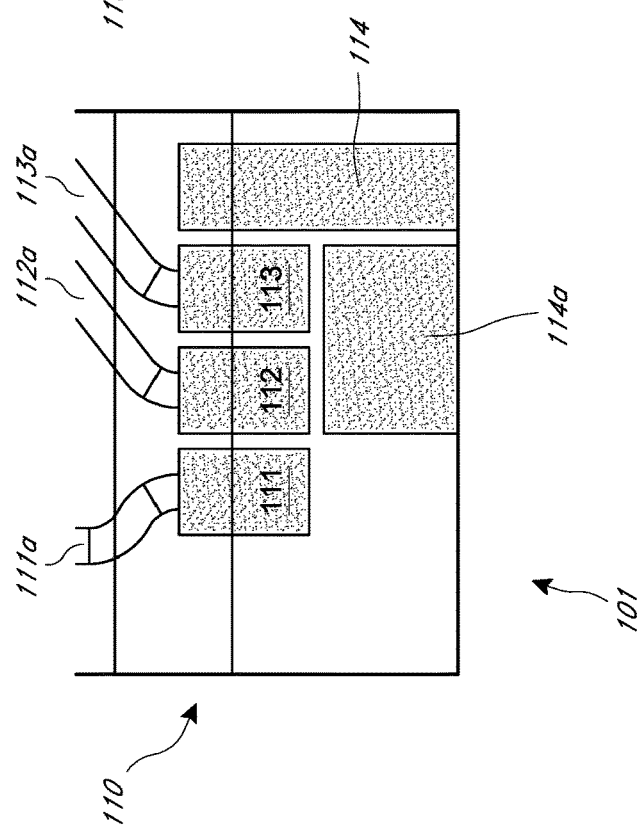

FIGS. 3A and 3B each depict a sensor 100 with an embodiment of a layout of five contacts: a working electrode contact 111, an auxiliary or counter electrode contact 112, a reference electrode contact 113, a sensor insertion contract 114, and a sensor identifier contact 114*a*. As shown, some of the contacts disposed on first end 101 may be spaced back from the edge of first end 101, for example, contacts 111, 112, 113. Other contacts may be disposed directly on the edge, for example, contacts 114, 114*a*. Moreover, in some embodiments, the lengths and widths of the contracts may vary from contact to contact. In some embodiments, greater than five or fewer than four contacts may be used.

Figure 4:
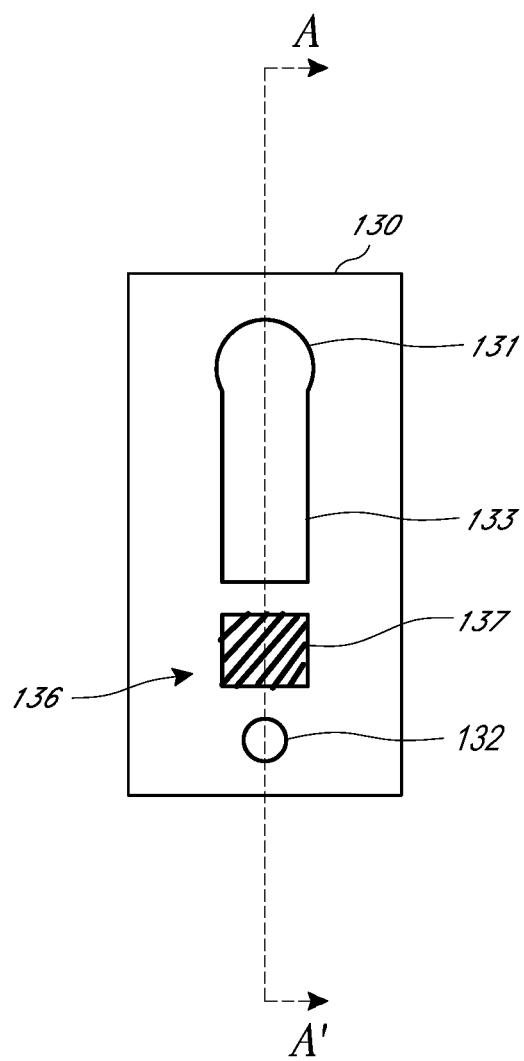
FIG. 4 depicts an embodiment of a second spacer layer including only a single reservoir space.

FIG. 4 depicts an embodiment of the second spacer layer 130 which does not include third sample reservoir space 135. Third sample reservoir space 135 is omitted and bridge 136 and reflector 137 have been enlarged. This will be described in greater detail below. In some embodiments, second spacer layer 130 may include a vent 132.

Figure 5B:
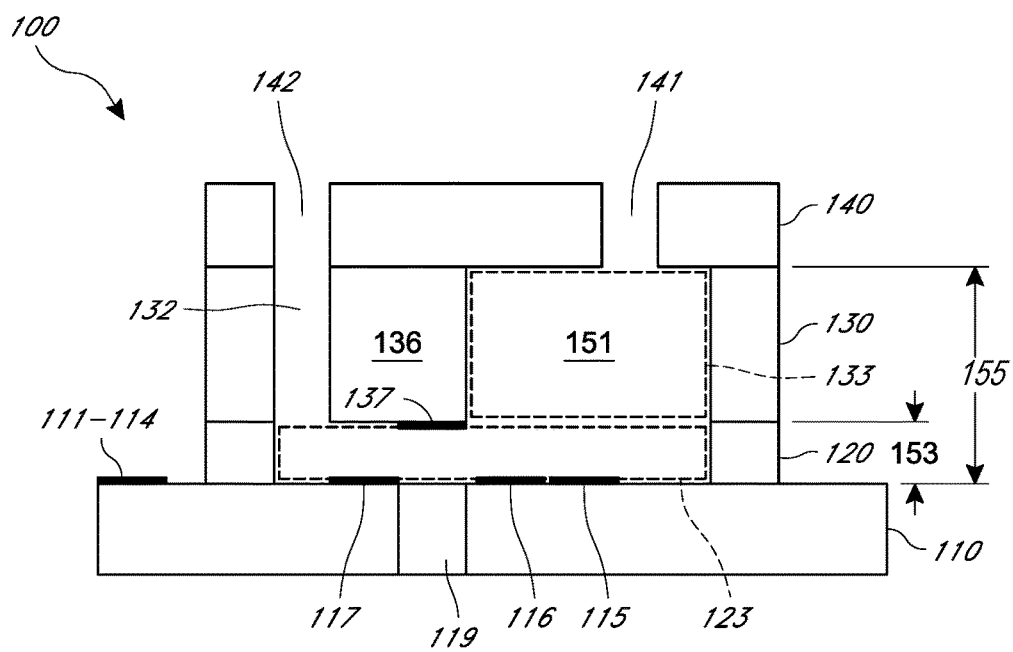

FIGS. 5A and 5B depict simplified (not to scale) longitudinal cross-sectioned views of embodiments of an assembled sensor 100 taken along the lines A-A' shown on the individual layers in FIGS. 2 and 4. As shown in FIG. 5A, the various layers of sensor 100 define an internal sample reservoir 151. The sample reservoir 151 includes the first sample reservoir space 123 (shown in dashed lines) defined at its lateral edges by first spacer 120, the second sample reservoir space 133 (shown in dashed lines), and the third sample reservoir space 135 (shown in dashed lines). The second sample reservoir space 133 and the third sample reservoir space 135 are both defined at their lateral edges by the second spacer layer 130. The thickness of first spacer layer 120 along with the thickness of the adhesive that binds this layer to the adjacent layers define the depth of the first reservoir space 123, which impacts the sensor's ability to be used for optical hemoglobin measurement. The thickness of the second spacer layer 130 defines the depth of the second sample reservoir space 133 and the third sample reservoir space 135.

The sample to be analyzed is introduced to sensor 100 at sample inlet 141, filling sample reservoir 151, including the first sample reservoir space 123, the second sample reservoir space 133, and the third sample reservoir space 135. Vent 142 is provided to prevent overfilling and to allow air to escape as sample reservoir 151 is filled.

In some embodiments, for example as shown in FIG. 5B, the third sample reservoir space 135 is omitted from second spacer layer 120, as shown in FIG. 4. The third sample reservoir space 135 may be omitted by extending bridge 136. Omitting the third reservoir space 135 may improve filling of the reservoir. Accordingly, sample reservoir 151 may comprise only first sample reservoir space 123 and second sample reservoir 133. A vent 132, 142 may also be included.

As shown in FIGS. 5A and 5B electrodes 115-117 are disposed on base layer 110 and are oriented so as to come into contact with a sample in sample reservoir 151. The bottom surface of bridge 136 of second spacer 130 may serve as a diffuse reflector 137, which is used in determining the hemoglobin concentration of the sample and will be more fully described below. Reflector 137 is disposed on bridge 136 of second spacer 130 at a location so as to be in contact with the sample in sample reservoir 151. Further, transmission window 119 is disposed on base layer 110 at a location substantially opposite the reflector 137. The transmission window 119 should allow light to pass there through from below sensor 100, reflect off reflector 137, and exit again through transmission window 119. It will be noted, that in some embodiments, base layer 110 is entirely formed from a transparent material.

The thickness of first spacer layer 120 along with the adhesive that bonds it to the adjacent layers defines a first depth 153 between the base layer 110 and the reflector 137. In some embodiments, first depth 153 is approximately 0.004 inches deep. First depth 153 is used to determine the effective path length for optical hemoglobin measurement, discussed in greater detail below. The combined thicknesses of the first spacer 120, second spacer 130, and adhesive layers that bind them together define a second depth 155.

Figure 6:
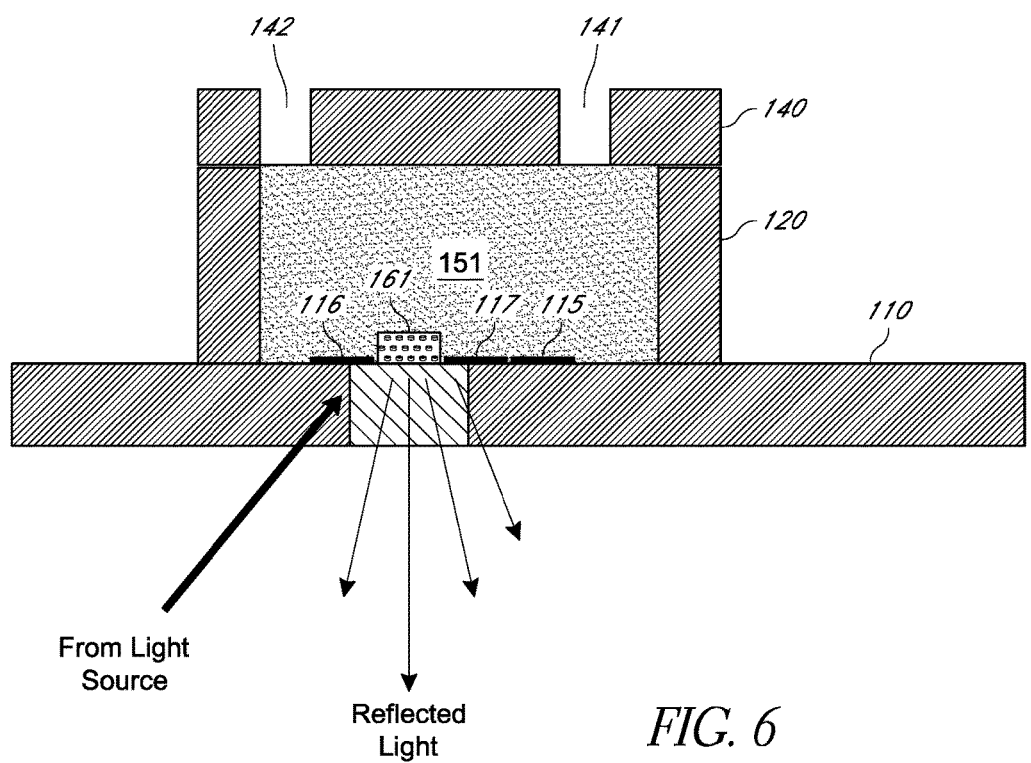
FIG. 6 depicts a simplified longitudinal cross-section view of an embodiment of a combination electrochemical lead and optical hemoglobin sensor.

FIG. 6 depicts a longitudinal cross-sectional view of an embodiment of sensor 100 that includes a deposit of porous, reflective material 161 on base layer 110. In some embodiments, a deposit of porous, reflective material 161 may be screen-printed directly on top of transmission window 119. The deposit of porous, reflective material 161 may be disposed between at least two of electrodes 115-117. In embodiments including a deposit of porous, reflective material 161, only a first spacer layer 120 need be used. Accordingly, these embodiments may omit second spacer layer 130 including bridge 136 and modify the thickness of the first spacer layer to be approximately 0.013 inches. The deposit of porous, reflective material 161 should be made with a material that can absorb the liquid sample and whose reflectance changes as the sample is absorbed. In some embodiments, the deposit of porous, reflective material 161 is formed from a porous paper, porous ink, or polymer filter material. The use of this embodiment in making an optical hemoglobin measurement will be discussed in greater detail below.

Figure 7:
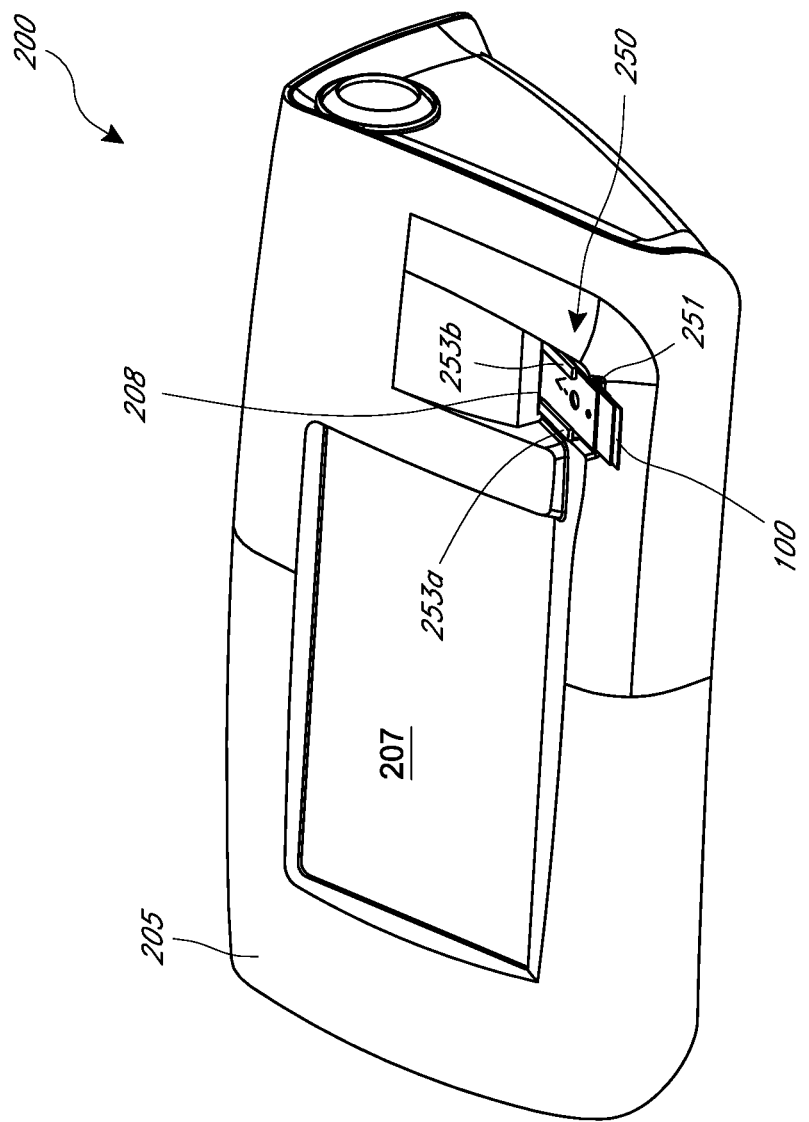
FIG. 7 depicts a perspective view of an embodiment of an analyzer with a combination electrochemical lead and optical hemoglobin sensor.

FIG. 7 depicts an embodiment of an analyzer configured to receive and analyze a sample on sensor 100. Sensor 100 is configured in size and shape to be insertable into an analyzer 200. The analyzer 200 may include a housing 205 configured in size and shape to be used on a tabletop or lab bench. In some embodiments, the housing 205 may be configured for hand held use. Housing 205 includes a display 207 that displays instructions and sample results to an operator. In some embodiments, the display 207 is an interactive display, such as a touch screen, which enables an operator to view, set, or select various analysis parameters and view sample results. In some embodiments, the analyzer 200 comprises an input device, such as a keyboard, soft or hard buttons, a mouse, or any other suitable input device which allows an operator to interact with the analyzer 200.

Housing 205 includes a sensor port 208 through which a sensor support structure 250 extends. Sensor port 208 may further be configured in size and shape to receive the first end 101 of sensor 100 through housing 205. The analyzer 200 may be configured with a single sensor port 208 to accept and analyze a single sensor 100 or with a plurality of sensor ports 208 to accept a plurality of sensors 100. A suitable analyzer for use in sampling blood lead levels is described in U.S. Pat. No. 5,873,990, entitled "Handheld Electromonitor Device," and in U.S. patent application Ser. No. 13/790,154, the entire contents of which are herein incorporated by reference.

As shown in FIG. 7, sensor support structure 250 extends through housing 205 at sensor port 208. Sensor support structure 250 includes a support surface 251 on which sensor 100 rests when inserted into analyzer 200. Further, sensor support structure 250 may further comprise sensor guides 253*a*, 253*b*, each of which may be configured to extend upward from support surface 251 and form a wall oriented in a direction parallel to a longitudinal axis of sensor 100 when sensor 100 is inserted into analyzer 200. Sensor guides 253a, 253b may further include an overhanging portion that covers at least a portion of a top surface of sensor 100 when sensor 100 is inserted. Sensor guides 253a, 253b and support surface 251 thus provide correct orientation and stability for sensor 100 as it is inserted into analyzer 200.

Figure 8:
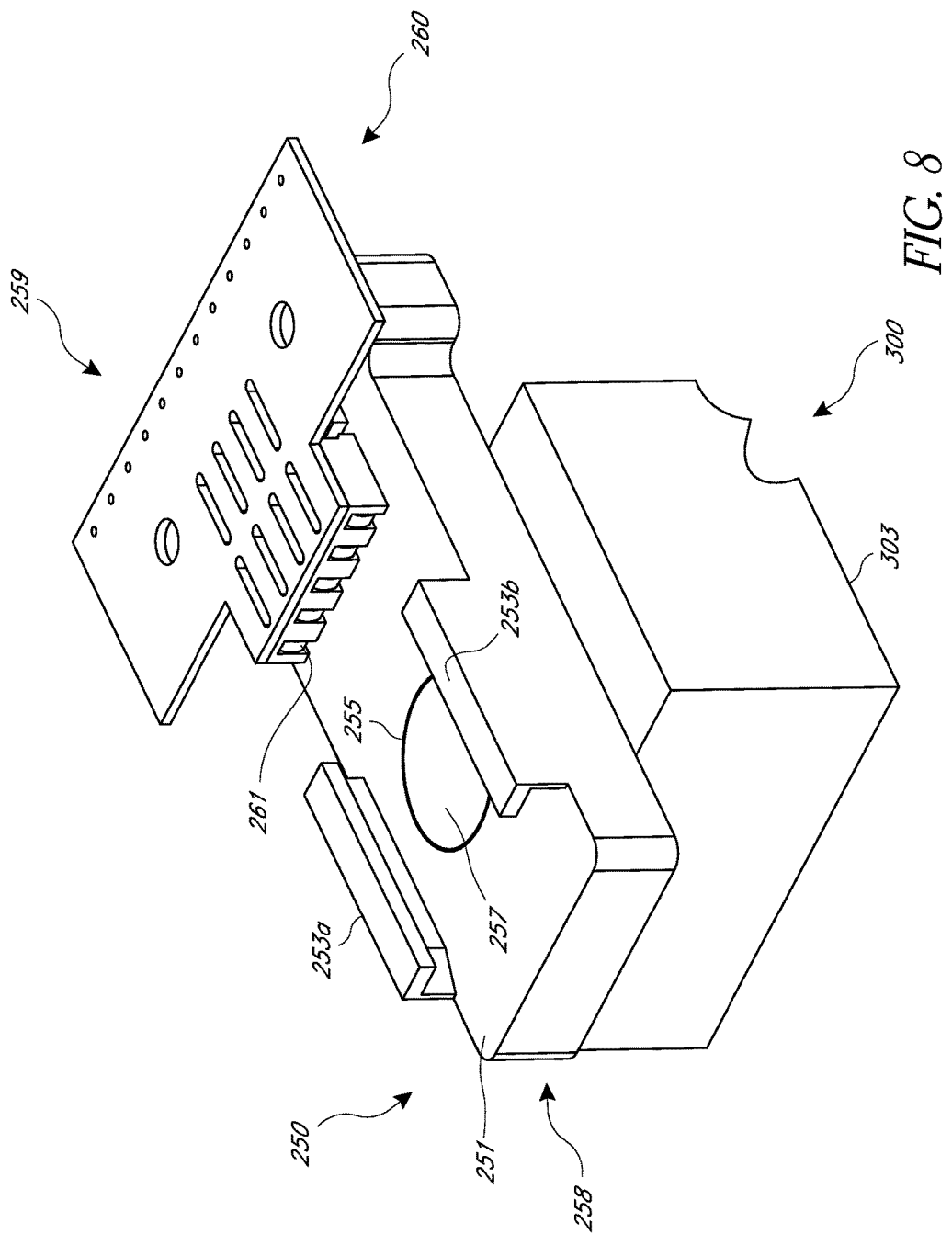
FIG. 8 depicts a perspective view of an embodiment of a sensor support structure and an optical system housing.

FIG. 8 depicts an embodiment of sensor support structure 250 removed from housing 205 for ease of description. Sensor support structure 250 includes an external end 258 (the portion extending through the housing 205 in FIG. 4) and an internal end 259, which is contained within the housing 205. Support surface 251 may comprise a substantially flat surface sized and shaped to support sensor 100 at an orientation that is substantially parallel to a surface on which analyzer 200 is resting. Sensor guides 253a, 253b extend upward from lateral sides of support surface 251. Internal end 259 may include a plurality of sensor contacts 261 disposed within an electrical contact structure 260. The plurality of sensor contacts 261 are positioned to contact the contacts 111-114 of sensor 100 when sensor 100 is inserted into sensor port 208. In some embodiments there is at least one sensor contact 261 for each of contacts 111-114 of sensor 100. In some embodiments, more than one sensor contact 261 may contact one of contacts 111-114. For example, in some embodiments, two sensor contacts 261 each make an electrical connection with contact 114 of sensor 100. In this way, contact 114 completes a circuit which signals analyzer 200 that a sensor 100 has been inserted.

Sensor support structure 250 may also comprise an aperture 255 which is formed as a hole extending through support surface 251. In some embodiments, aperture 255 may be filled with a window 257. Aperture 255 is positioned on the sensor support structure to correspond to the transmission window 119 formed in the base layer 110 of the sensor 100. In this way, when a sensor 100 is inserted into the sensor port 208, an optical path is created between the transmission window 119 and the aperture 255 through which an optical signal can pass.

The window 257 is made from a scratch resistant material that permits light of the wavelengths discussed below to pass there through. In some embodiments, window 257 may comprise glass, transparent polycarbonate plastic, or other suitable material. Some embodiments may advantageously use a material with a high index of refraction, for example, materials with a refractive index greater than 1.4. When materials with higher indices of refraction are used, incoming light that enters the window at a shallow angle will be refracted at a steeper angle, thus contacting and reflecting off reflector 137 at the steeper angle. The angles discussed in this paragraph are measured between the ray of light and an axis normal to the surface of reflector 137. Angles approaching 0 degrees are considered steeper while angles approaching 90 degrees are considered shallower. In some embodiments, the window 257 may comprise a sapphire window.

An optical system 300 is also shown in FIG. 8 and is disposed substantially below sensor support structure 250 and within housing 205. In some embodiments, optical system 300 comprises an optical system housing 303. Aperture 255 extends through support surface 251 and into optical system housing 303.

Figure 9:
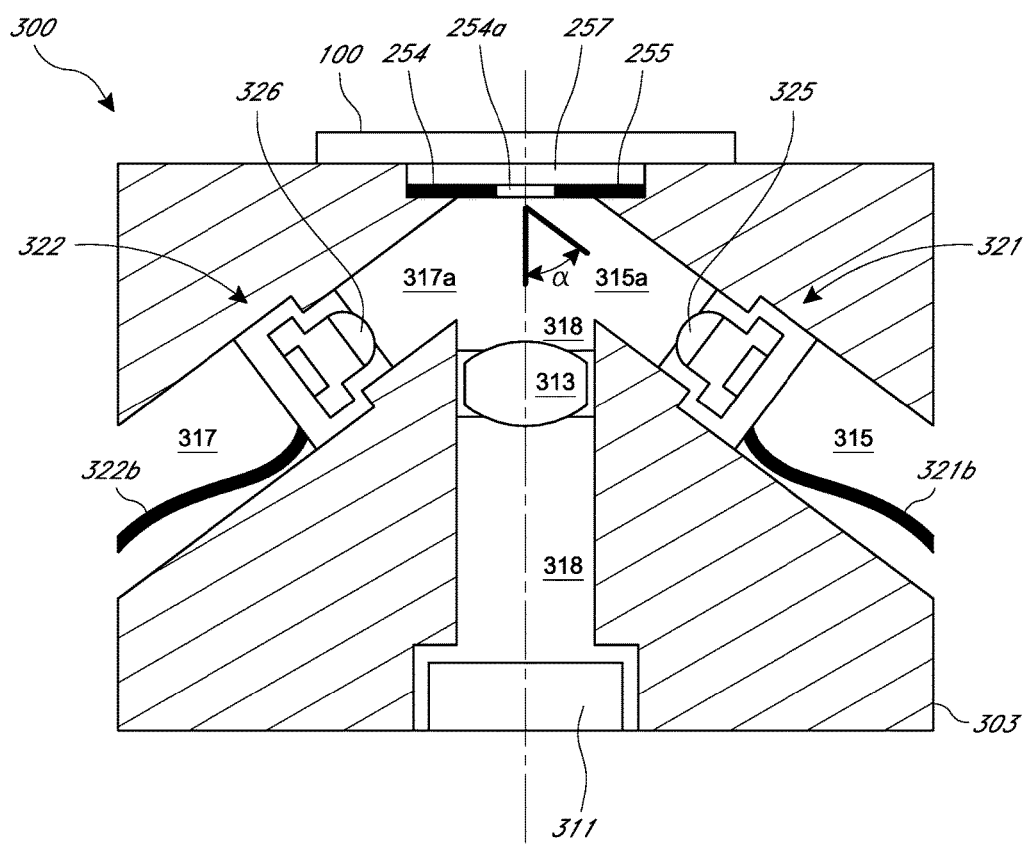
FIG. 9 depicts a cross-sectional view of an embodiment of an optical analyzer.

Optical system 300 is now described in greater detail with reference to FIGS. 9-10. FIG. 9 depicts a cross-sectional view of an embodiment of an optical housing 303 and the various components that may be contained therein. Optical system 300 includes first and second light sources 321, 322, collection lens 313, and detector 311 all disposed within housing 303. In some embodiments, the optical system 300 may include only a single light source (for example, light source 321 or light source 322), or more than two light sources. However, the following description presents a non-limiting example that includes two light sources. First and second light sources 321, 322 may also include corresponding electrical connections 321a, 322a for powering and controlling the first and second light sources. In some embodiments, the optical system 300 may include only a single light source. In some embodiments, the first and second light sources 321 and 322 comprise a single LED or LED chip. In some embodiments, the first and second light sources 321 and 322 comprise one or more LED chips. In some embodiments, the first and second light sources 321 and 322 comprise 4 LED chips located symmetrically about the longitudinal axis of the first channel 315.

A first source channel 315 may be formed as a hole extending through optical system housing 303. The first source channel 315 may extend between the first light source 321 and the aperture 255. In some embodiments, first source channel 315 includes a narrow portion 315a, wherein the narrow portion 315a comprises a diameter smaller than the diameter of first source channel 315 where the first light source 321 is disposed. First light source 321 is disposed within first channel 315 and oriented so that a central axis of the light emitted from first light source 315 is substantially coaxial with a longitudinal axis of first channel 315. In some embodiments, the central axis of the light emitted from the first light source 315 is not coaxial with the longitudinal axis of the first channel, and is arranged so that at least a portion of the emitted light travels the length of the longitudinal axis of the first channel 315 and exits through the aperture 255. In some embodiments, first light source 321 is disposed within first source channel 315 at a position below narrow portion 315a. A second source channel 317 may be formed as a hole extending through optical system housing 303 similar to the first source channel 315. The second source channel 317 may extend between the second light source 322 and aperture 255. In some embodiments second source channel 317 includes a narrow portion 317a, wherein the narrow portion 317a comprises a diameter smaller than the diameter of second source channel 317 at the location of the second light source 322. Second light source 322 is disposed within second channel 317 and oriented so that a central axis of the light emitted from second light source 317 is coaxial with a longitudinal axis of second channel 317. In some embodiments, second light source 322 is disposed within second source channel 317 at a position below narrow portion 317a. In some embodiments, the first channel 315 and the second channel 317 may be oriented such that the longitudinal axes of the first channel 315 and the second channel 317 are perpendicular to each other. In some embodiments, the longitudinal axes of the first channel 315 and the second channel 317 may intersect, forming an acute or obtuse angle.

A collection channel 318 is also disposed within housing 303 and is formed as a hole extending between aperture 255 and a bottom surface of housing 303. Collection channel 318 is disposed below aperture 255 and has a longitudinal axis that extends in a direction normal to the plane of aperture 255. Detector 311 is disposed in or below collection channel 318 on the end of collection channel 318 opposite aperture 255. Detector 311 may comprise a photo diode with an integral amplifier, a photomultiplier or another optical detector capable of measuring light intensity. In some embodiments, a collection lens 313 is disposed in collection channel 318 between detector 311 and aperture 255. Collection channel 318 or optical housing 303 may include a mounting structure for securing collection lens 313. Collection lens 313 is oriented and configured in size and shape to focus light traveling from the aperture 255, through collection channel 318 onto detector 311. An angle α is formed between each of the longitudinal axes of first and second source channels 315, 317 and the longitudinal axis of collection channel 318. In other words, α is the angle between how a light source 321, 322 is aimed and an axis extending normal to the detector 311. In some embodiments, α is approximately 45°. In some embodiments, a is approximately 10°, 15°, 20°, 25°, 30°, 35°, 40°, 50°, 55°, 60°, 65°, 70° 75°, 80°, 85°, 90°, or more, or any angle there between. It should be understood, however, that the value of α affects the reflectance of light emitted by the first light source 321 and the second light source 322 as the light passes through the aperture 255 and through the sample in the first sample reservoir space 123. In some embodiments, the angle α of the longitudinal axes of the first channel 315 and the second channel 317 may be the same as each other, or may be different. For example, the angle α for the first source channel 315 may be approximately 45°, and the angle α for the second source channel 317 may be other than 45°. It will be noted that while first and second channels 315, 317 and collection channel 318 have all been depicted as lying in the same plane in FIG. 9, this may not be the case for all embodiments.

In some embodiments, a washer 254 may be an aperture, such as a structure including a center hole 254a may be disposed below or attached to the underside of window 257 in aperture 255. Washer 254 with center hole 254a may be configured to narrow the beam of light passing through aperture 255. In some embodiments, washer 254 is made from plastic, rubber, or metal and may be finished with a flat (non-glossy) non-reflective surface.

Figure 10:
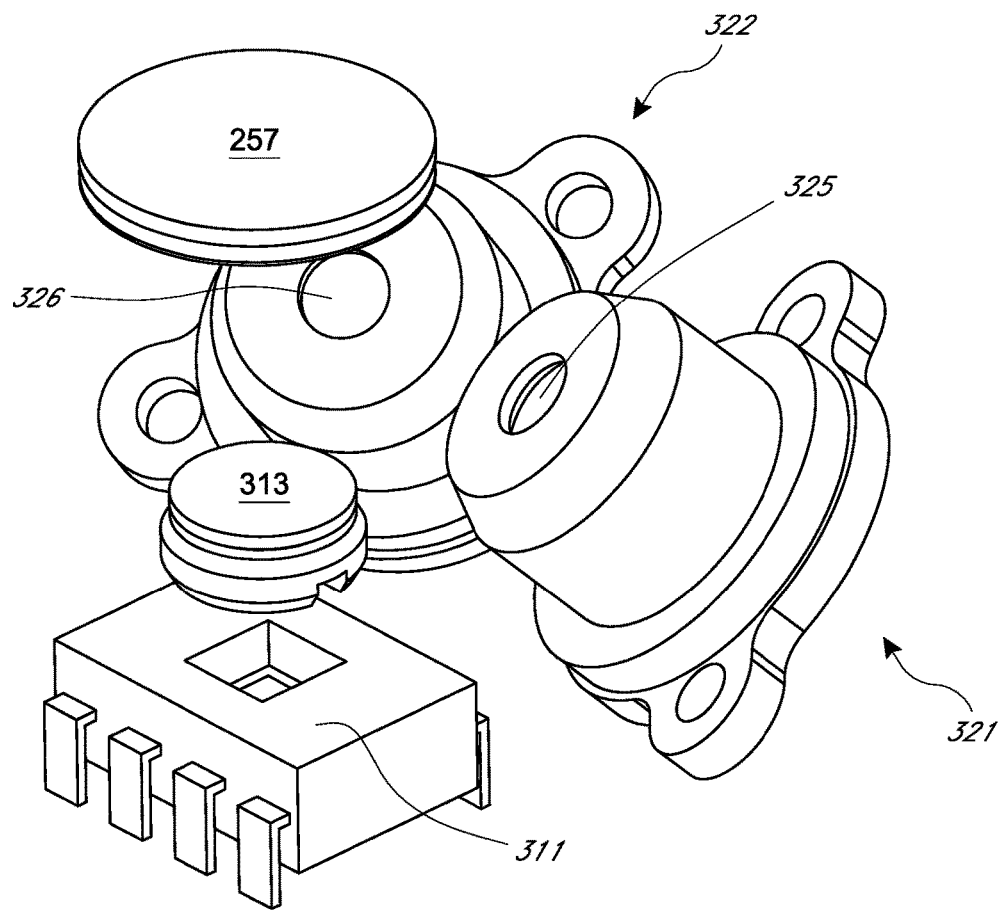
FIG. 10 depicts a perspective view of an embodiment of components of an optical system with the optical system housing removed.

Some of the components of an embodiment of an optical system 300 can be seen more clearly in FIG. 10, which depicts a perspective view of an embodiment of an optical system 300 with the optical system housing 303 removed. Optical system 300 includes first light source 321 and second light source 322. In some embodiments, the first and second light sources 321, 322 include integrated lenses 325, 326 which are configured to focus the light emitted through aperture 255 and onto reflector 137 of sensor 100. Each of the first and second light sources 321, 322 may comprise a plurality of LEDs positioned on a printed circuit board. In some embodiments, each of the first and second light sources 321, 322 comprise four LEDs positioned on a printed circuit board. It will, however, be understood by one of skill in the art that a single LED or other light source may be used. Additionally, in some embodiments a single light source 321 may be used or more than two light sources may be used.

The light sources 321, 322 may be configured to emit light with an approximately 405 nm wavelength, the benefits of which will be discussed below. In some embodiments, the wavelength may be about 410 nm. In some embodiments, the wavelength may be from about 350 nm to about 450 nm. In some embodiments, the wavelength can be between 250 nm and 950 nm. It will be understood by one of skill in the art that other wavelengths of light can be used.

Figure 11:
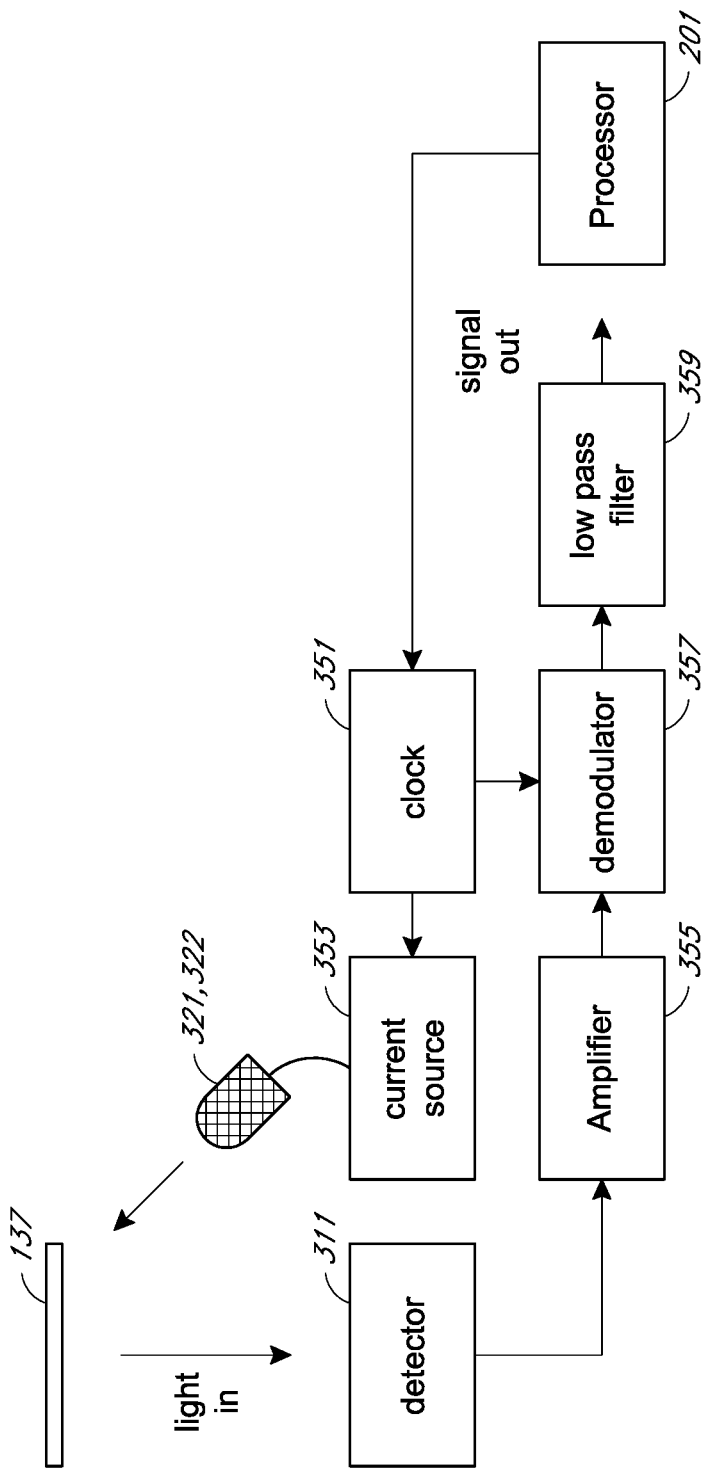
FIG. 11 depicts a simplified view of an embodiment of the operation of an optical system capable of lock-in detection.

In one embodiment, optical system 300 includes the electronic components illustrated schematically in FIG. 11. A time base generator or clock 351 is electrically connected to a current source 353 such that an output of clock 351 is an input to current source 353. Current source 353 is then electrically connected to first and second light sources 321, 322. Detector 311 is electrically connected to an amplifier 355 such that an output of the detector 311 is an input of the amplifier 355. Amplifier 355 is further electrically connected to a demodulator 357 such that an output of amplifier 355 is a first input of demodulator 357. Demodulator 357 is also electrically connected to the clock 351 such that an output signal from clock 351 is a second input of demodulator 357. In some embodiments, demodulator 357 is electrically connected to a low pass filter 359 such that an output of demodulator 357 is an input of low pass filter 359. Low pass filter 359 may then be electrically connected, either directly or indirectly, to a processor 201. Processor 201 may be connected to and control the clock 351. In some embodiments, more than one (for example, two), low pass filters may be used. For example, a first low pass filter may have a larger time constant (in other words, a slower response) and be used during measurement of a filled sensor, and a second low pass filer may have a shorter time constant (in other words, a faster response) and be used during a reference measurement taken while the sensor is being inserted (as will be described below in greater detail in reference to FIG. 16). The processor 201 may select between the two low pass filters in this example. Processor 201 may control all the components depicted in FIG. 11, and may further control the operations of the analyzer 200. Processor 201 may comprise more than one processor.

The arrangement of components shown in FIG. 11 and described above may provide improved lock-in signal processing in some embodiments of optical system 300. The output signal of clock 351 may be used to drive current source 353 at a particular frequency. Current source 353 will then, accordingly, drive the first and second light sources 321, 322 such that they flash at the frequency indicated by clock 351. The light from first and second light sources 321, 322 passes through the sample and is reflected off reflector 137. At least a portion of the light reflected off reflector 137 travels through the sample again, toward the aperture 255, is received by detector 311. The detector 311 converts the optical signal into an electrical output signal. The output of detector 311 is amplified at amplifier 355 and fed as a first input to demodulator 357. Demodulator 357 also receives, as a second input, the output of the clock. Accordingly, demodulator 357 is able to distinguish the portion of light received at the detector 311 due to light emitted from light sources 321, 322 at the frequency of the clock 351, or at a frequency having a known deviation from the frequency of the clock 351 from light received at the detector 311 from other ambient sources, which has a frequency other than that of the clock 351 or other than the known deviation from the frequency 351 of the clock. The demodulator removes substantially any signal from the electrical output which does not correspond to light emitted at the frequency of the clock 315. In some embodiments, the LEDs are flashed at approximately 100 Hz, 500 Hz, 1 kHz, 1.5 kHz, 2 kHz, 5 kHz, 10 kHz, 50 kHz, or more, or any value there between; it will be understood by one of skill in the art and according to the principles taught here, that other frequencies may be used without departing from the scope of this disclosure.

Sensor 100 and analyzer 200 can be used to make simultaneous measurement of blood lead and hemoglobin concentration as follows. First, a sensor 100 is inserted into analyzer 200 at port sensor port 208. Contact 114 comes into contact with sensor contacts 261 of analyzer 200 completing a circuit within analyzer 200 that signals that sensor 100 has been inserted. Analyzer 200 may determine whether a sensor has been inserted according to the methods disclosed in U.S.

patent application Ser. No. 13/790,154, entitled "Apparatus and Method for Analyzing Multiple Samples," which has been previously incorporated by reference above.

Analyzer 200 may further perform routines to ensure that the sensor 100 that has been inserted has not previously been used. Accordingly, analyzer 200 may check to ensure that the sensor 100 has been wetted. If a wetted sensor has been inserted, analyzer 200 may provide an error message indicating that a previously used sensor has been inserted. This will prompt the user to discard the old sensor and insert a fresh one. This determination may also be made with the methods disclosed in U.S. patent application Ser. No. 13/790,154. As used herein, the term "wetting the sensor" is used to indicate introducing a sample, such as a blood sample that may be prepared with a reagent, to the sensor and a "wetted sensor" indicates a sensor wherein the sample has been introduced.

At this point, analyzer 200 may provide a user with prompts on display 207 giving the user an option of which tests should be performed. The user may select blood hemoglobin concentration, blood lead concentration, or both. In another embodiment, the sensor may be programed to automatically test for both blood hemoglobin and blood lead concentration and no prompts will provided to the user.

If a blood hemoglobin concentration will be performed, analyzer 200 will take an optical reference measurement, for example, of the empty sensor 100 prior to introduction of the prepared sample. This reference measurement will be discussed in greater detail below.

Analyzer 200 may then prompt the user to introduce the prepared sample into the sensor 100 that has been inserted into analyzer 200. The user may prepare the sample by mixing the blood sample with a solution of hydrochloric acid, which reagent prepares the sample for an electrochemical lead concentration measurement as discussed elsewhere. The user may then transfer the prepared sample to sensor 100 with a pipette or dropper, introducing the prepared sample at sample inlet 141 filling sample reservoir 151. Analyzer 200 may again check whether the sensor 100 has been wetted using the methods indicated above. Once analyzer 200 determines that the sample has been introduced, hemoglobin concentration and blood concentration analysis may begin.

Blood hemoglobin concentration analysis will be described first; however, this analysis may proceed simultaneously with the blood lead concentration analysis described below.

Figure 12:
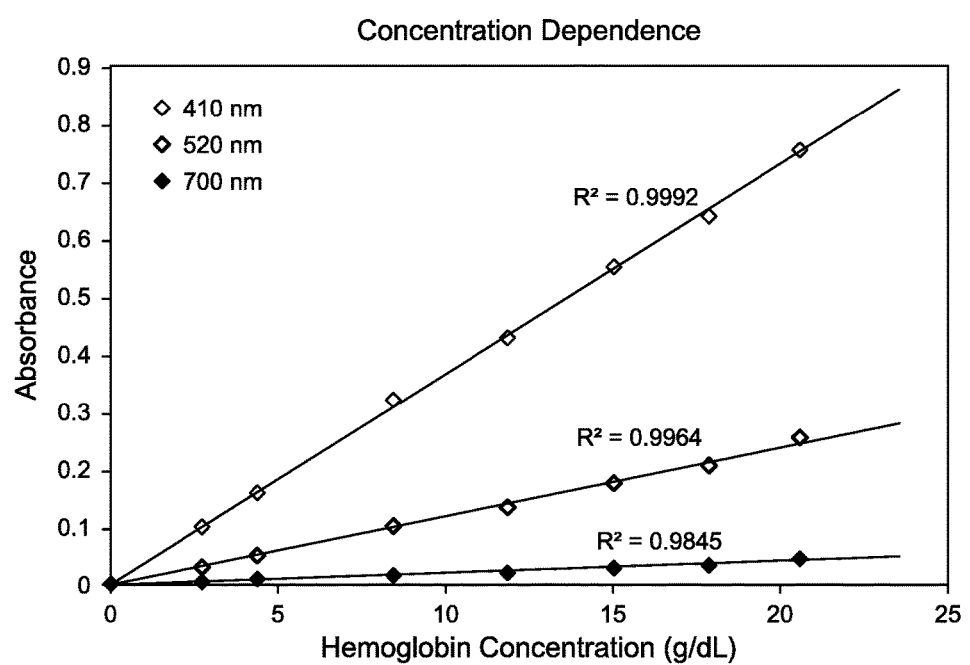
FIG. 12 is a graph showing a linear relationship between optical absorbance and hemoglobin concentration at three light wavelengths.

The optical absorbance of blood treated with hydrochloric acid depends on the hemoglobin concentration of the sample. For example, FIG. 12 depicts three correlation curves obtained experimentally using a commercial UV/Vis spectrophotometer. As shown, absorbance measurements of prepared samples were taken at three light wavelengths, 410 nm, 520 nm, and 700 nm, each yielding a substantially linear relationship between the hemoglobin concentration (measured in g/dL) and the absorbance of the sample. This linear relationship can be described using the Beer-Lambert Law:

$$\text{Concentration}=\text{Absorbance}/(\varepsilon \times \text{path}) \qquad [1]$$

Absorptivity, $\varepsilon$, is a property of hemoglobin. Path is the length of the sample through which a beam of light is passed and can be obtained from the linear dimension of the cuvette in which the sample is contained, and the Absorbance can be calculated as follows:

$$\text{Absorbance}=-\log(I/I_0) \qquad [2]$$

I is the measured intensity of light passing through the sample cuvette and $I_0$ is the intensity of a reference beam, which can be obtained by passing the light through a reference cuvette. The reference cuvette may be empty or may contain a liquid that does not include any hemoglobin, for example.

Figure 13:
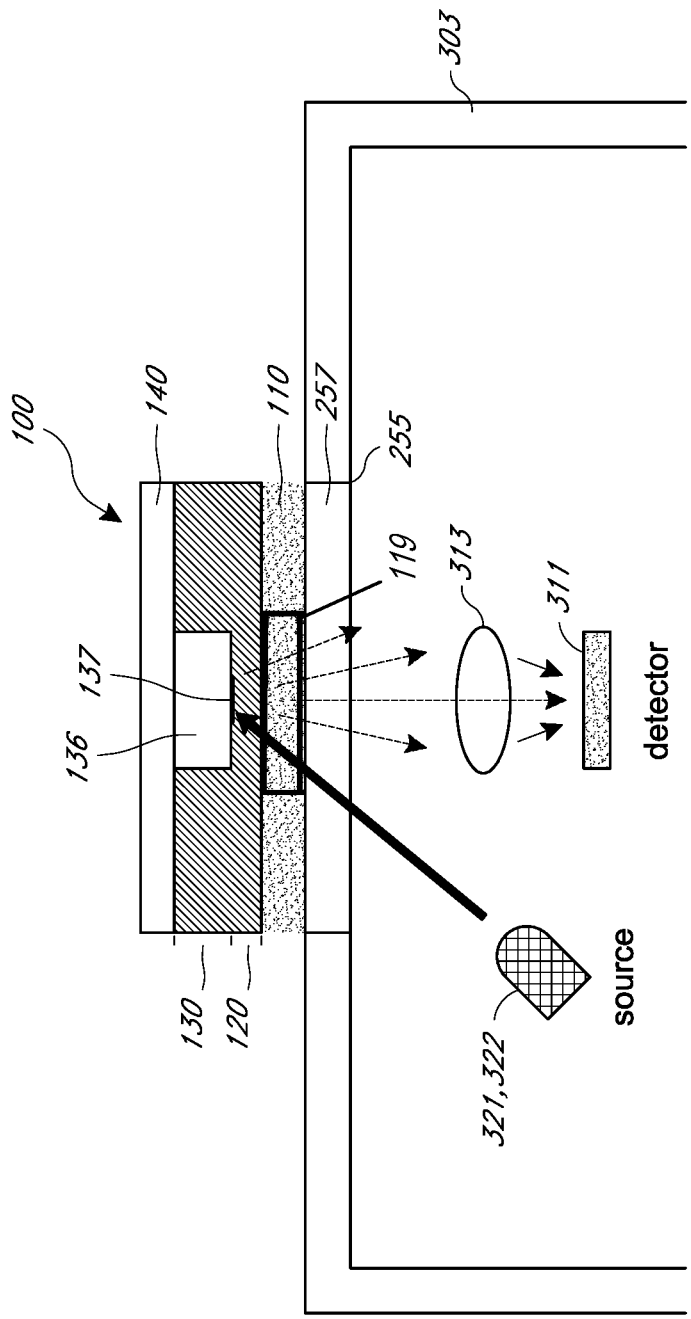
FIG. 13 depicts a simplified view of the operation of an embodiment of an optical system.

These general principles may be modified and implemented in analyzer 200 as follows to allow analyzer 200 to optically determine the hemoglobin concentration of the prepared sample using a reflectance measurement. Optical system 300 may be configured with the various components discussed above to allow it to measure the intensity of the light reflected off reflector 137 or off a deposit of porous, reflective material 161. The discussion below will provide an example of a sensor 100 including a reflector 137; similar principles apply by analogy, to embodiments of sensor 100 including a deposit of porous, reflective material 161. As shown in FIG. 13, first and second light sources 321, 322 emit light upward toward the reflector 137 of sensor 100. In some embodiments, first and second light sources 321 and 322 emit light simultaneously, and in some embodiments, the first and second light sources 321 and 322 alternately emit light. In some embodiments, first and second light sources 321, 322 are pulsed at approximately 1 kHz as described above. To reach reflector 137, the light travels upward through the aperture 255 in optical system housing 303 and window 257. The light continues through the transmission window 119 of base layer 110 of sensor 100 and passes through the sample in sample reservoir 151 until some fraction of it is diffusely reflected downwards off reflector 137. A portion of the reflected light travels out through the aperture 255 into the collection channel 318, where it is focused with collection lens 313 towards detector 311. Detector 311 measures the intensity of the light received. The intensity signal may then be converted to an electrical signal and input to processor 201 of analyzer 200 and used to calculate the hemoglobin concentration.

First depth 153, defined by the thickness of first spacer layer 120 and discussed above with reference to FIGS. 5A and 5B, should be sufficiently thin so as to ensure that some light is reflected back out of sensor 100. If first depth 153 is overly deep, substantially all of the light entering sensor 100 through transmission window 119 will be absorbed by the sample and nothing will be reflected and measured. This effect can be minimized by ensuring that first depth 153 is sufficiently thin, for example, about 0.004" or by increasing the intensity of the light emitted from first and second light sources 321, 322.

Figure 14:
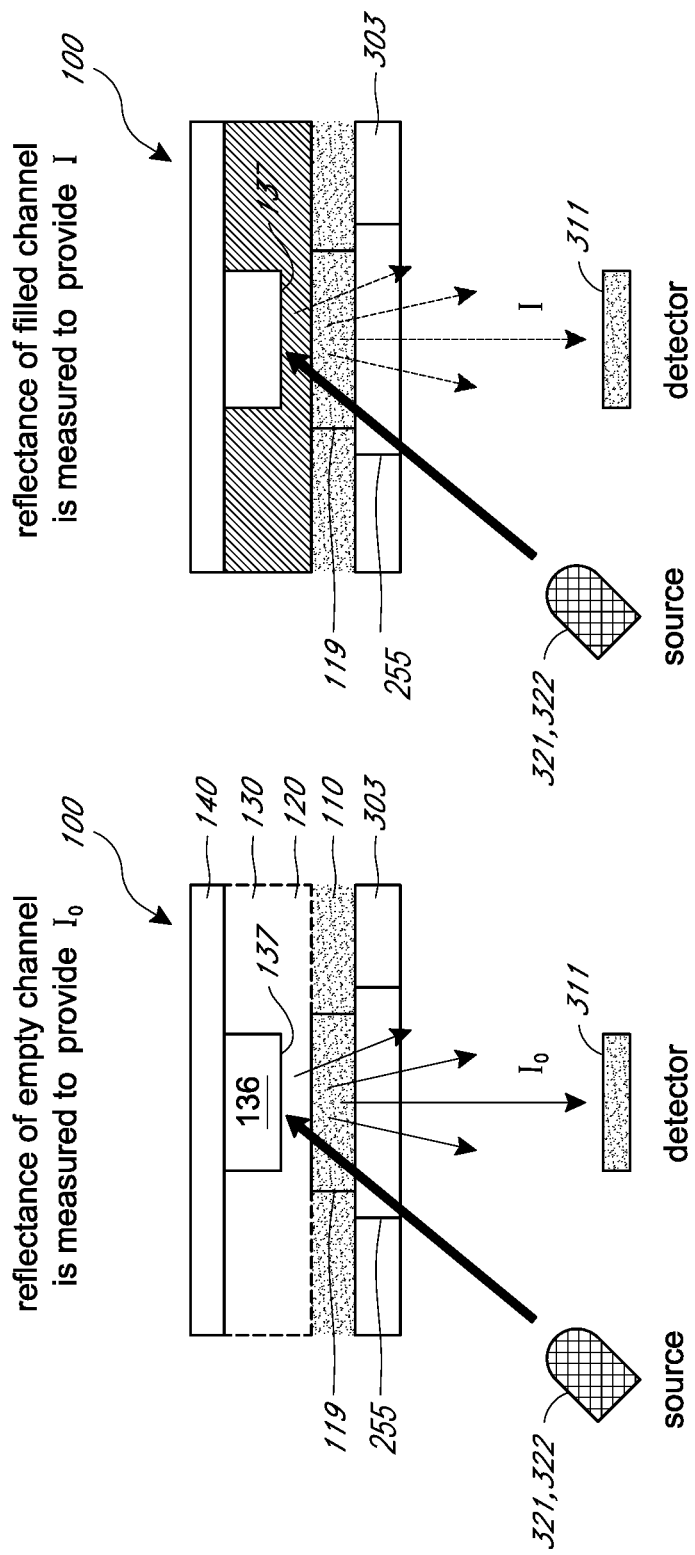
FIG. 14 depicts exemplary optical measurements of a sensor in both filled and empty states.

As shown in FIG. 14, optics system 300 may first take a reference scan of sensor 100 before the sample has been introduced to generate reference intensity measurement, $I_0$. The sample may then be introduced and optical system 300 can take a second measurement, yielding the measured intensity of light reflected through the sample, I. Reflectance can then be calculated using the following equation:

$$\text{Reflectance}=-\log(I/I_0) \qquad [3]$$

The same sensor 100 can be used for each measurement, with a first measurement being taken while the sensor is empty and a second measurement taken after the sample is introduced to the sensor. In other embodiments, however, two sensors, with similar dimensions and optical characteristics, may be used: a first empty sensor and a second filled sensor; this will, however, yield less accurate results due to variations in sensor dimensions due to manufacturing and variations of sensor positioning within the analyzer.

Figure 15:
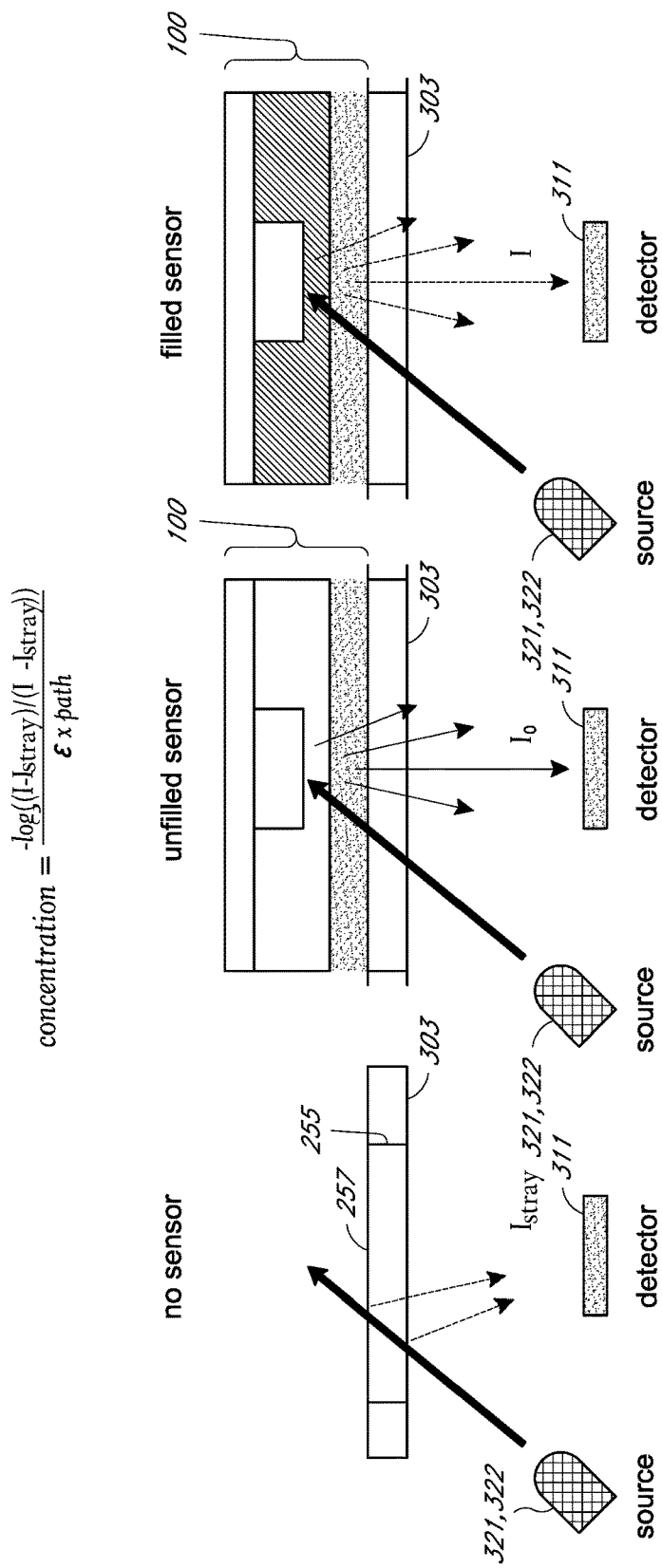
FIG. 15 depicts optical measurements taken with no sensor in place, with an empty sensor in place, and with a filled sensor in place.

In some embodiments, analyzer 200 with optical system 300 may further be calibrated to account for internally reflected stray light or any contribution from any fluorescence produced by the substrate of sensor 100 to achieve more precise and consistent results. As shown in FIG. 15, some light reflected off internal components of optical system 300 may be received at detector 311. To correct for this stray light, reflectance measurement may be adjusted as follows:

$$\text{Reflectance} = -\log((I - I_{stray})/(I_0 - I_{stray})) \quad [4]$$

The internally reflected stray light, $I_{stray}$, can be estimated by taking a measurement with no sensor in place. This measurement can then be subtracted from the measurements taken of the filled and unfilled sensor.

Figure 16:
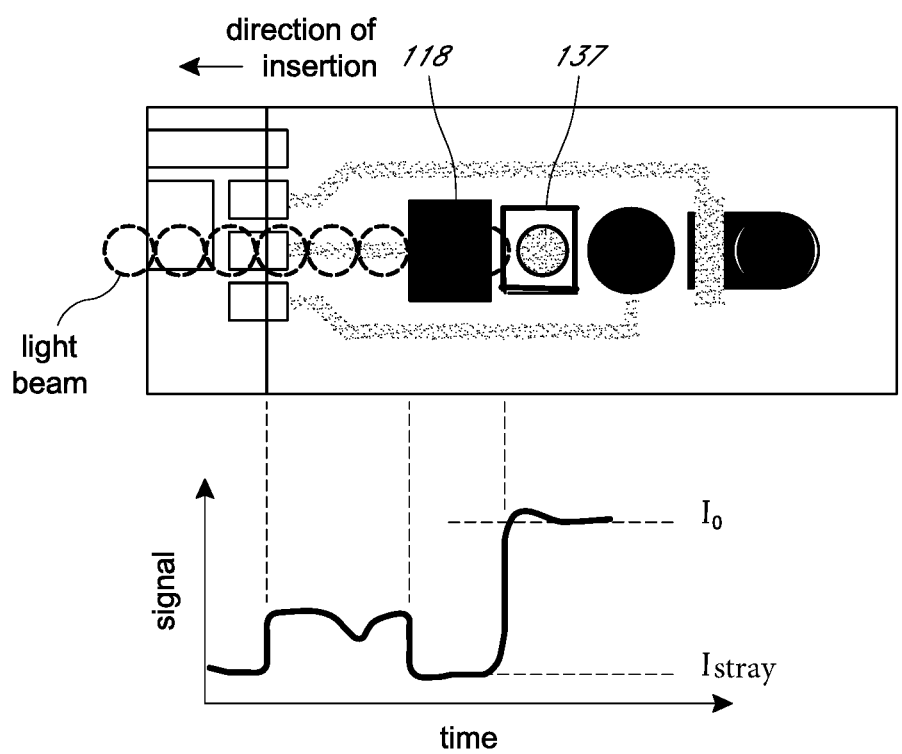
FIG. 16 is a graph of an example of a measured reflectance signal taken as a sensor is inserted into the analyzer.

Alternatively, the internally reflected stray light, $I_{stray}$, can be estimated by measuring the reflected signal from a light-absorbing black surface on sensor 100 as sensor 100 is inserted into or withdrawn from analyzer 200. This embodiment is depicted in FIG. 16, which shows how the measured intensity of reflected light varies as sensor 100 is inserted into analyzer 200. As the sensor is inserted, it moves across the light beam emitted from optical system 300. As shown in FIG. 16, as the beam passes over a light-absorbing black surface 118 the measured intensity falls to a level representing the internally reflected stray light, $I_{stray}$. Once the sensor is fully inserted, the beam is focused on reflector 137 yielding a value representing I if the sensor is filled or $I_0$ if the sensor is empty. In some embodiments, the light-absorbing black surface 118 may be the carbon of the counter electrode 117. In other embodiments it may be a coating applied to the bottom surface of base layer 110. The width of the light-absorbing black surface 118 may be adjusted to provide for a more accurate measurement of $I_{stray}$ as the sensor is inserted. In some embodiments, the width of the light-absorbing black surface 118 is between 1-5 millimeters. In some embodiments, the width of the light-absorbing black surface 118 is between 3.5-4 mm. In another embodiment, the internally reflected stray light, $I_{stray}$, is estimated by taking the difference between the two methods previously described—in other words, by taking the difference between a measurement of a reference cuvette and a measurement of a light-absorbing black surface. Experimentally, this difference has been found to provide an accurate estimate of the internally reflected stray light, $I_{stray}$.

In some embodiments, measurements for $I_0$ and $I_{stray}$ can be obtained by mechanically moving a sample white surface and a sample black surface into contact with the optical system and measuring the reflectance.

Figure 17:
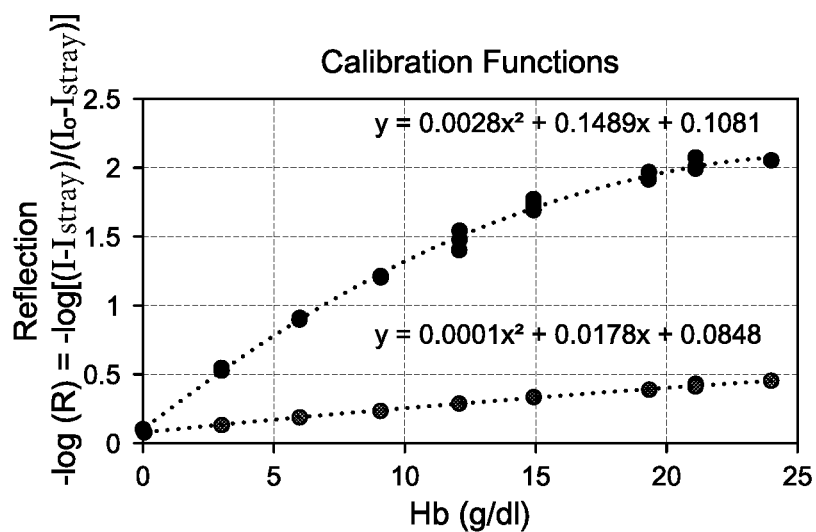
FIG. 17 is a graph depicting two non-linear curves relating measured reflectance to hemoglobin concentration.

The reflectance measured and calculated using equation [3] or corrected equation [4] above does not give a linear relationship between reflectance and hemoglobin concentration of the sample. Nonetheless, a nonlinear calibration curve can be calculated that will allow analyzer 200 to determine hemoglobin concentration from reflectance using the measurement of reflectance described above. Two nonlinear example calibration curves are shown in FIG. 17. In the figure, calibration curves for light with wavelengths of 405 nm and 625 nm are shown as second degree polynomials. One of skill in the art will appreciate that other functions, other than second degree polynomials, may be used.

Figure 18:
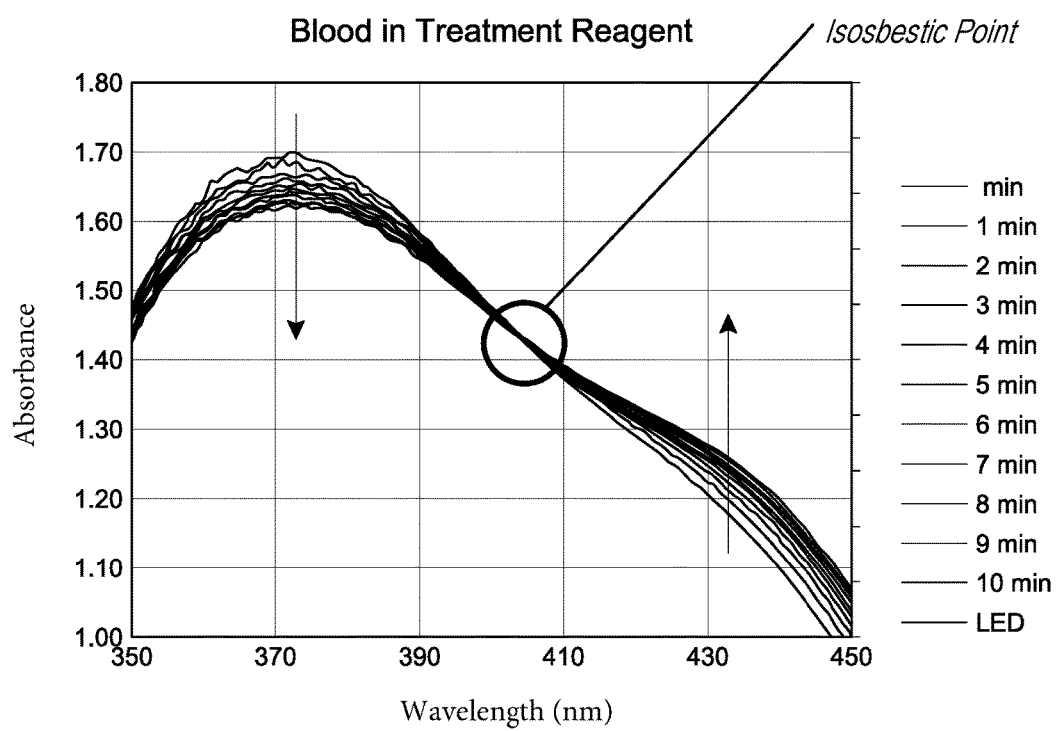
FIG. 18 is a graph which indicates how the absorbance of a treated blood sample may change over time when measured optically at different wavelengths of light.
Figure 19:
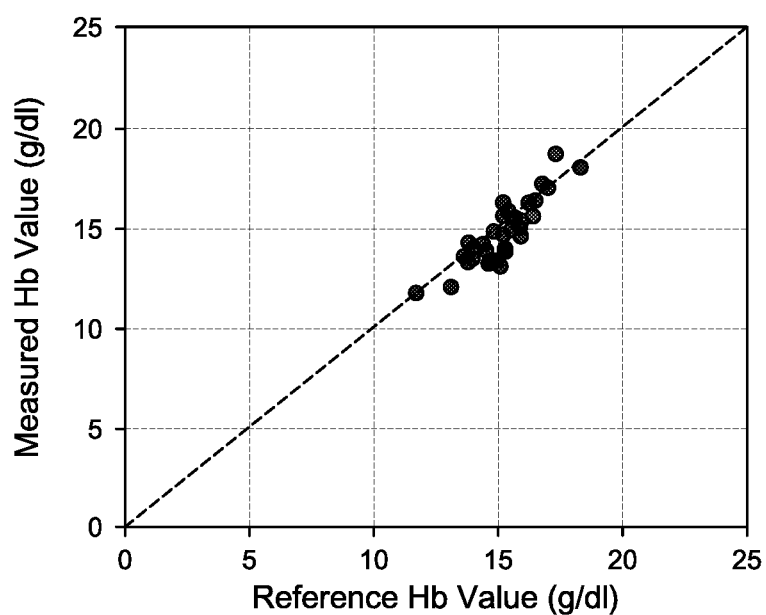
FIG. 19 is a graph comparing the results of optical hemoglobin measurements taken using the principles of the present disclosure with reference measurements.

The wavelength of light in the measurement may also affect the accuracy of the analysis. As noted above, first and second light sources 321, 322 may use light with a wavelength between 250 nm and 950 nm. The inventors have observed that the absorbance or reflectance of a blood sample treated with hydrochloric acid change over time. For example, a sample treated with hydrochloric acid and measured immediately may yield a different absorbance or reflectance value than the same sample measured again 10 minutes later. It has further been observed that change over time of the absorbance or reflectance of a sample is also affected by the wavelength of light used to make the measurement. These results can be seen in FIG. 18 which shows the measured absorbance of a treated sample measured with wavelengths of light between 350 nm and 450 nm with measurements taken every minute for ten minutes. As can be seen in FIG. 18, at wavelengths less than approximately 405 nm, the measured absorbance decreases over time. At wavelengths greater than approximately 405 nm, this trend reverses and the measured absorbance increases over time. Importantly, the inventors have observed that at approximately 405 nm, the absorbance does not change over time, indicating an isosbestic point. Accordingly, because the time between preparation of the sample and measurement of the sample may vary, it is preferred to configure analyzer 200 to measure with light of approximately 405 nm. In some embodiments, analyzer 200 may measure at a number of wavelengths in addition to 405 nm and use the additional information to improve the precision of the measurement.

The apparatus and methods disclosed herein for making an optical hemoglobin measurement of a treated blood sample may be modified to allow for measurement with different geometries. For example, throughout this application, reference has been made to optically measuring for hemoglobin concentration using a light source and detector positioned generally below the sensor wherein the light from the light source passes upward through the sample and is reflected back down to the detector. This is merely exemplary. One of skill in the art will understand, according to the principles herein disclosed, that the light source and detector could be positioned generally above the sensor. In some embodiments, the light source may be positioned on one side of the sensor and the detector could be positioned on the opposite side of the sensor such that the light emitted travels through a transparent portion of the lid or through a hole in the lid, through the sample, and through a transparent portion on the base of the sensor.

In addition to the blood hemoglobin concentration previously described, analyzer 200 may also be configured to simultaneously measure blood lead concentration using the same sensor 100. Blood lead concentration analysis can be performed electrochemically using sensor 100 and analyzer 200 as described in U.S. Pat. No. 5,368,707, entitled "Convenient Determination of Trace Lead in Whole Blood and Other Fluids," the entire contents of which is herein incorporated by reference, and U.S. Pat. No. 5,468,366, entitled "Colloidal-Gold Electrosensor Measuring Device," mentioned previously above.

Upon completion of the hemoglobin and lead concentration analyses, analyzer 200 may display the results of the analysis to the user via display 207. Alternatively, results may be stored, sent to an external computer, or printed.

Accordingly, the embodiments and principles described above may be used to measure the lead and hemoglobin concentrations in a blood sample simultaneously, using a single sensor and analyzer.

Example Hemoglobin Measurement

A sensor and analyzer incorporating the above-described principles for optically measuring hemoglobin has been developed and tested yielding the following results. The analyzer was configured to calculate hemoglobin concentration using the 405 nm calibration curve shown in FIG. 15:

$$y=-0.0028x^2+0.1489x+0.1081 \qquad [5]$$

where y represents the reflectance calculated as $-\log((I-I_{stray})/(I_0-I_{stray}))$, and x represents the hemoglobin concentration with units of g/dL.

Forty whole blood samples were obtained by venipuncture and stored at refrigerated temperature for less than 72 hours prior to analysis. Fifty microliters of blood sample were added to one tube of Magellan Diagnostics LeadCare treatment reagent, mixed thoroughly for one minute and introduced into a sensor. The light intensity at 405 nm reflected from the sensor was measured before ($I_0$) and after (I) the sample was introduced. The concentration of hemoglobin was determined using the calibration curve presented above. The same samples were tested using an Instrumentation Laboratories GEM Premier 4000 co-oximeter to obtain a reference value for comparison. As shown in FIG. 18, there is an excellent correlation between the hemoglobin concentration determined using the principles herein disclosed and the reference value.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the embodiments disclosed herein should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting.

What is claimed is:

1. A method for measuring an analyte in a liquid sample, the method comprising:
    flowing a liquid sample into a reservoir of a sensor, the reservoir comprising a first portion comprising a first depth and a second portion comprising a second depth that is greater than the first depth, wherein the reservoir is bounded by a first side and a second side such that the liquid sample within the reservoir is positioned between the first side and the second side;
    determining a measurement of the analyte in the liquid sample by:
        illuminating the liquid sample in the first portion of the reservoir through a transparent portion of the sensor, wherein the transparent portion of the sensor is on the first side of the first portion of the reservoir;
        determining a reflectance of the liquid sample based on a measurement of light reflected off a reflector positioned on the second side of the first portion of the reservoir, wherein light for illuminating the sample passes through the transparent portion on the first side of the reservoir, through the liquid sample in the reservoir, and is reflected off the reflector on the second side of the reservoir; and
        determining the measurement of the analyte based on the determined reflectance.

2. The method of claim 1, wherein the reflectance is determined by comparing a measured intensity to a reference intensity.

3. The method of claim 2, further comprising measuring the reference intensity by:
    illuminating an empty sensor; and
    measuring a reflectance of the empty sensor.

4. The method of claim 2, further comprising:
    measuring internally reflected stray light by detecting the intensity of light reflected from a light absorbing surface on the sensor;
    subtracting the measured internally reflected stray light from the reference intensity and the measured intensity.

5. The method of claim 4, wherein measuring the internally reflected stray light comprises measuring the internally reflected stray light by detecting the intensity of light reflected from a light absorbing surface on the sensor as the sensor is inserted into or withdrawn from an analyzer.

6. The method of claim 1, further comprising measuring a second analyte in the liquid sample using an electrode positioned within the reservoir of the sensor.

7. The method of claim 6, wherein the electrode is positioned within the second depth of the reservoir.

* * * * *